US011950762B2

(12) United States Patent
Koizumi et al.

(10) Patent No.: US 11,950,762 B2
(45) Date of Patent: Apr. 9, 2024

(54) ELECTRONIC ENDOSCOPE SYSTEM AND DATA PROCESSING DEVICE

(71) Applicant: HOYA CORPORATION, Tokyo (JP)

(72) Inventors: Ryohey Koizumi, Tokyo (JP); Yosuke Ikemoto, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 605 days.

(21) Appl. No.: 17/283,417

(22) PCT Filed: Apr. 10, 2020

(86) PCT No.: PCT/JP2020/016068
§ 371 (c)(1),
(2) Date: Apr. 7, 2021

(87) PCT Pub. No.: WO2020/218029
PCT Pub. Date: Oct. 29, 2020

(65) Prior Publication Data
US 2021/0338043 A1   Nov. 4, 2021

(30) Foreign Application Priority Data

Apr. 26, 2019   (JP) ................. 2019-086464

(51) Int. Cl.
*G06T 1/00*   (2006.01)
*A61B 1/00*   (2006.01)
*A61B 1/06*   (2006.01)

(52) U.S. Cl.
CPC ...... *A61B 1/0005* (2013.01); *A61B 1/000094* (2022.02); *A61B 1/0661* (2013.01)

(58) Field of Classification Search
CPC ............ A61B 1/0005; A61B 1/000094; A61B 1/0661; A61B 1/05; A61B 1/0669;
(Continued)

(56) References Cited

U.S. PATENT DOCUMENTS

| 7,599,533 B2 * | 10/2009 | Nishimura | ............ G06T 7/0012 |
| | | | 382/209 |
| 2012/0155731 A1 * | 6/2012 | Weersink | ................ G06T 7/344 |
| | | | 382/128 |

(Continued)

FOREIGN PATENT DOCUMENTS

| JP | 2016-120026 | 7/2016 |
| WO | 2017/057680 | 4/2017 |

(Continued)

OTHER PUBLICATIONS

May 27, 2023 Chinese Office Action in corresponding Chinese Appl. No. 202080005742.7 and partial machine translation thereof.

(Continued)

*Primary Examiner* — Charlotte M Baker
(74) *Attorney, Agent, or Firm* — GREENBLUM & BERNSTEIN, P.L.C.

(57) ABSTRACT

This electronic endoscope system includes an evaluation value calculation unit, an assessment unit, and a representative value determination unit. The evaluation value calculation unit is configured so as to obtain an evaluation value indicating an extent of a lesion in biological tissue in each of a plurality of images captured in a predetermined section along the depth direction of a region in an organ. The assessment unit is configured so as to assess whether the extent of the lesion in the section is changed on the basis of the degree of variation of the evaluation value. The representative value determination unit is configured so as to define a representative value of the section representing the evaluation value, in a different method when the extent of the lesion is assessed to be changed and when the extent of the lesion is assessed not to be changed.

16 Claims, 14 Drawing Sheets

(58) Field of Classification Search
CPC ........... A61B 1/0684; A61B 1/07; G06T 1/00; G06T 7/00
USPC ....................................................... 382/128
See application file for complete search history.

(56) References Cited

U.S. PATENT DOCUMENTS

2018/0279866 A1  10/2018  Makino
2019/0244351 A1   8/2019  Dolnik et al.
2020/0107699 A1   4/2020  Ariyoshi

FOREIGN PATENT DOCUMENTS

WO    2018/002935    1/2018
WO    2018/230130   12/2018

OTHER PUBLICATIONS

Official Communication issued in International Bureau of WIPO Patent Application No. PCT/JP2020/016068, dated Jun. 23, 2020.

* cited by examiner

ELECTRONIC ENDOSCOPE SYSTEM AND DATA PROCESSING DEVICE

TECHNICAL FIELD

The present invention relates to an electronic endoscope system and a data processing device that process images of biological tissue in an organ.

BACKGROUND ART

Lesion parts in biological tissue have varying levels of severity, from inflammation in which a mucosal layer of the biological tissue becomes thin, rough, and red, to ulcers that are partially missing from the mucosal layer and a lower layer thereof. For example, an ulcer part of a lesion of an ulcerative colitis (UC) is white with white moss and purulent mucus, and an inflammation part is reddish with edema and easy bleeding. Such a lesion part can be captured and observed by an endoscope system.

However, in order for a surgeon to be able to distinguish between a normal part and the lesion part by the difference in color included in the endoscopic image, it is necessary to undergo long-term training under the guidance of an expert. Moreover, it is not easy for an experienced surgeon to identify the lesion part with a slight color difference, so careful work is required. Therefore, it is preferable that the endoscope system provides an evaluation result in which an extent of a lesion in the lesion part is objectively quantified.

On the other hand, an endoscope system that can suppress fluctuations in an evaluation value of an inflammation part to perform a stable calculation of the evaluation value and suppress a processing load of the calculation of the evaluation value has been known (Patent Literature 1).

CITATION LIST

Patent Literature

Patent Literature 1: WO 2017/057680 A

SUMMARY OF INVENTION

Technical Problem

The above-described endoscope system includes a light source device that irradiates illumination light toward a subject, an image acquisition unit that is obtained by capturing an image of reflected light from the subject with an image sensor and acquires a color image including at least three or more color components, and an evaluation unit that obtains evaluation results for target diseases of each pixel based on an angle formed by a line segment connecting a predetermined reference point set in a color plane and pixel corresponding points in the color plane of each pixel constituting the color image acquired by the image acquisition unit and a reference axis with a correlation to the target disease, within the color plane defined by at least two of at least three color components. The reference axis is set so as to pass through a predetermined reference point. The reference axis is at least one of an axis having a correlation with a target disease whose degree of inflammation is equal to or less than a predetermined value and an axis having a correlation with a target disease whose degree of inflammation is equal to or greater than a predetermined value in the color plane.

According to such a configuration, it is possible to suppress the fluctuations in the inflammation evaluation value due to the brightness of the image, perform the stable calculation of the inflammation evaluation value, and suppress the processing load of the calculation of the inflammation evaluation value.

However, the brightness of the image changes depending on the photographing conditions such as a distance between the subject and the endoscope, and even if a site of biological tissue having the same strength of inflammation is captured, the inflammation evaluation value varies. On the other hand, the inflammation evaluation value also fluctuates even when an extent of a lesion is changed along a depth direction in the organ, and variations occur. In the above endoscope system, it is difficult to understand whether the variation in the inflammation evaluation value is due to the brightness of the image or due to the change in the extent of the lesion, and it is difficult to determine whether the extent of the lesion is changed in the depth direction. Depending on whether the extent of the lesion is changed, a method of treating a lesion part may also be different.

Therefore, an object of the present invention is to obtain an indicator that appropriately indicates an extent of a lesion within a predetermined region in an organ in an electronic endoscope system and a data processing device that process an image of biological tissue inside the organ.

Solution to Problem

One aspect of the present invention is an electronic endoscope system including an endoscope configured to capture an image of biological tissue in an organ spreading in a depth direction and a processor configured to process the captured image of biological tissue. The electronic endoscope system includes an evaluation value calculation unit configured to obtain an evaluation value indicating an extent of a lesion in biological tissue of each of a plurality of images captured within a predetermined section along a depth direction of a region in the organ, an assessment unit configured to assess whether the extent of the lesion is changed in the section based on a degree of variation of the evaluation value, and a representative value determination unit configured to define a representative value of the section representing the evaluation value in a different method when it is assessed that the extent of the lesion is assessed to be changed and when the extent of the lesion is assessed not to be changed.

The assessment unit may be configured to perform the assessment using an indicator indicating the degree of variation obtained from the evaluation value, and when the degree of variation indicated by the indicator is equal to or greater than a predetermined value, assess that the extent of the lesion is changed in the section.

The indicator may be a difference between a maximum value and a minimum value among the evaluation values.

The indicator may be a standard deviation or variance of the evaluation value.

The indicator may be an indicator indicating a degree of fit of regression lines in which the evaluation values are regressed in the order of the captured images.

The electronic endoscope system may further include a position information processing unit configured to associate information on the image-captured position in the organ, in which each of the images is captured, with each of the images, in which the assessment unit may further use the information on the image-captured position to specify the region in the section where the extent of the lesion is changed.

The evaluation value obtained by the evaluation value calculation unit may be an evaluation value indicating the extent of the lesion of the biological tissue of each of the plurality of images captured in each of the plurality of sections obtained by dividing the region in the organ including the section in depth directions, and the electronic endoscope system may further include a section specifying unit configured to specify a section in which the image is captured among the plurality of sections by using the information on the image-captured position.

The assessment unit may be configured to assess each section, and the representative value determination unit may be configured to define the representative values for each section.

The electronic endoscope system may further include the position information processing unit configured to associate the information on the image-captured position in the organ, in which each of the images is captured, with each of the images, in which the assessment unit may be configured to perform the assessment using an inclination of the regression line in which the evaluation value is regressed to the image-captured position, and when the inclination is equal to or greater than a predetermined value, assess that the extent of the lesion is changed in the section.

The assessment unit may further use the indicator indicating the degree of fit of the regression line to perform the assessment, and when the degree of fit indicated by the indicator exceeds a predetermined value, perform the assessment using the inclination of the regression line.

The assessment unit may be configured to specify the degree of change in the lesion in the section according to a size in the inclination of the regression line.

The assessment unit may be configured to perform the assessment based on a variation in some of the evaluation values.

The representative value determination unit may be configured so that when it is assessed that the extent of the lesion is changed in the section, the maximum value of the evaluation value of at least some of the images captured in the section among the evaluation values becomes the representative value of the section.

The representative value determination unit may be configured so that when the extent of the lesion is assessed not to be changed in the section, any one of the average value, a most frequent value, and a median value of the evaluation value of at least some of the images captured in the section among the evaluation values becomes the representative value of the section.

The electronic endoscope system may further include a monitor configured to display information on the assessment result of whether the extent of the lesion is changed on a screen in a different display mode when the extent of the lesion is assessed to be changed and when the extent of the lesion is assessed not to be changed.

Another aspect of the present invention is a data processing device that processes an image of biological tissue in an organ that extends in a depth direction. The data processing device includes an evaluation value calculation unit configured to obtain an evaluation value indicating an extent of a lesion in biological tissue of each of a plurality of images captured within a predetermined section along a depth direction of a region in the organ, an assessment unit configured to assess whether the extent of the lesion is changed in the section based on the degree of variation of the evaluation value, and a representative value determination unit configured to define a representative value of the section representing the evaluation value in a different method when the extent of the lesion is assessed to be changed and when the extent of the lesion is assessed not to be changed.

Advantageous Effects of Invention

According to the electronic endoscope system and data processing device described above, it is possible to obtain the indicator appropriately indicating the extent of the lesion within the predetermined region in the organ.

DESCRIPTION OF EMBODIMENTS

Figure 1:
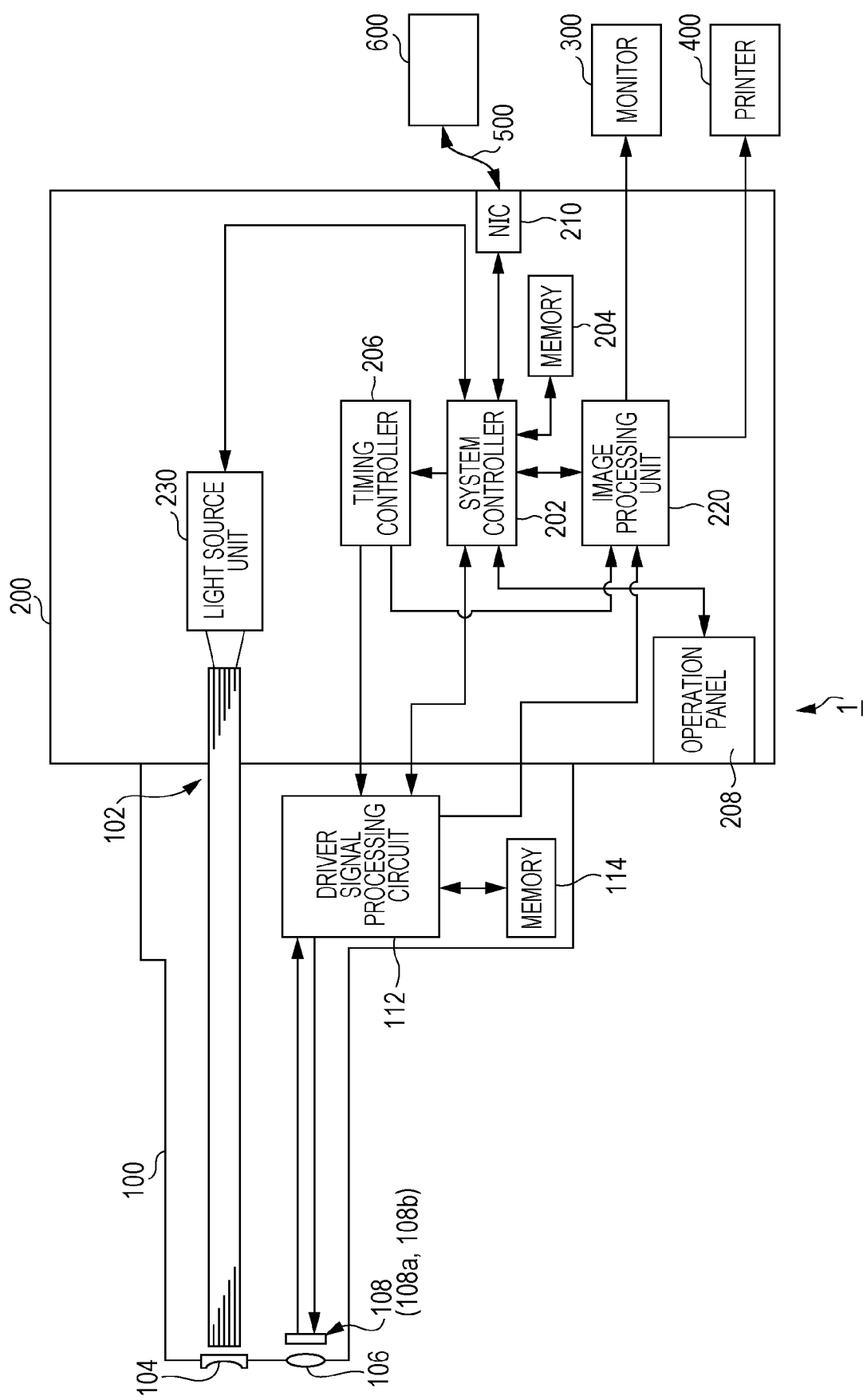
FIG. 1 is a block diagram illustrating a configuration of an endoscope system according to an embodiment.

Hereinafter, before explaining an electronic endoscope system and a data processing device of an embodiment of the present invention with reference to the drawings, first, an evaluation of an extent of a lesion inside an organ will be conceptually described.

(Summary of Evaluation of Extent of Lesion Inside Organ)

A processor of an electronic endoscope system of an embodiment described below processes an image of biological tissue inside an organ captured by an electronic endoscope to evaluate an extent of a lesion. The extent of the lesion includes at least strength of a lesion, and according to an embodiment, further includes the spread of the lesion. When capturing an image of the biological tissue inside the organ, for example, the electronic endoscope is inserted from an opening end of a tubular organ to a position of a deepest portion to be captured in a depth direction inside the organ, and captures an image of the biological tissue inside the organ while continuously moving from the position toward the opening end of the organ. The depth direction includes both a direction from the opening end to the deepest portion and a direction from the deepest portion to the opening end.

The captured image of the biological tissue may be a moving image continuously captured at regular time intervals, or may be a plurality of still images captured intermittently while moving the electronic endoscope in the organ. When moving the electronic endoscope, the speed of the electronic endoscope does not necessarily have to be constant, and the electronic endoscope can return to the location where the electronic endoscope has passed and captures the image, that is, the moving direction thereof can also be partially reversed. Note that in an embodiment, in the case of the moving image, the electronic endoscope performs capturing while moving in substantially the same direction at substantially the same speed.

In the evaluation of the extent of the lesion, the processor calculates image evaluation values (evaluation value) indicating strength of a lesion in each of the plurality of images of biological tissue illuminated with white illumination light. The image evaluation value is not particularly limited, but when the lesion is inflammation, examples thereof can include a inflammation value obtained by evaluating a degree of inflammation of a lesion part (inflammation part) based on information on a color component of the lesion part (for example, red).

The organ to be evaluated is not particularly limited, and examples thereof can include a digestive tract such as pharynx to esophagus, stomach, duodenum, a small intestine, and a large intestine.

Further, for example, the biological tissue is illuminated with special light including fluorescence of 445 to 700 nm in which a phosphor is emitted with a laser beam having a wavelength of 405 nm, a laser beam having a wavelength of 445 nm, and a laser beam having a wavelength of 445 nm, and captured, a ratio of two image signals from three RGB image signals obtained by the capture is created, and evaluation values for each image created by using a processing result of performing predetermined enhancement processing on these two image signals, for example, evaluation values for evaluating a mucous membrane or the like in atrophic gastritis can also be used as the image evaluation values.

Further, for example, the biological tissue is illuminated and captured by using light having a wavelength of 600 nm, light having a wavelength of 630 nm, and light having a wavelength of 540 nm as illumination light, and the evaluation values for each image created by using the processing result of performing the predetermined enhancement processing on the image obtained by the capturing, for example, the evaluation values for evaluating a condition of blood vessels in a deep portion of the mucous membrane can also be used as the image evaluation values.

In addition, cells in a mucous membrane of a digestive tract, which are illuminated with light and are pretreated by staining, are enlarged and captured, and such as an average value of a feature quantity (shape information such as a length, a diameter, a perimeter, and roundness) of a cell nucleus, an evaluation value for evaluating an extent of a lesion such as non-tumor, adenoma, and cancer, and the like can also be used as the image evaluation value.

Further, the image evaluation value may be an evaluation value such as a Mayo score obtained for each image. In this case, the evaluation value calculated by using the evaluation device machine-learned from the captured image may be used as the above image evaluation value. Further, the image evaluation value may be a value obtained by quantifying a histopathological evaluation for each image.

The processor calculates a representative evaluation value (representative value) of the image evaluation value from image evaluation values of a plurality of images that are obtained by capturing an image of biological tissue in a predetermined section along a depth direction of a region in the captured organ, and evaluates the extent of the lesion in the predetermined section using the representative evaluation value. The section to be evaluated may be one section in the organ, but according to an embodiment, it is preferable that the region in the organ is divided into a plurality of sections in the depth direction. In this case, when each image is captured, the information on the image-captured position inside the captured organ is associated with each image. Further, according to an embodiment, it is preferable to include the lesion evaluation unit configured to evaluate the extent of the lesion using a representative evaluation value. Specifically, the processor evaluates the spread and strength of lesions that are continuously spreading in the depth direction of the organ using the representative evaluation values calculated for each of the plurality of sections obtained by dividing the region in the image-captured organ in the depth direction by using the acquired information on the image-captured position. In the following description, a case where the representative evaluation values are calculated for each of the plurality of sections using the information on the image-captured position and the strength and spread of the lesion are evaluated as the extent of the lesion will be described as an example.

Here, the section is a section divided by a distance equal to or greater than a sampling interval of the image-captured position. According to an embodiment, this section is a section divided at a predetermined interval. The predetermined interval may be a constant interval or may not be constant. Further, the predetermined interval may change at any time during the calculation of the representative evaluation value. For example, sections divided at fine intervals in advance may change to a larger section, for example, a segment which is a part that can be identifiably distinguished from other parts in an organ.

According to an embodiment, the evaluation of the extent of the lesion includes obtaining the representative evaluation values of the image evaluation values corresponding to each of the plurality of sections, displaying a distribution of the representative evaluation value in the depth direction, or providing a total value of the representative evaluation values corresponding to the sections including the lesion part that is assessed using the image evaluation values. As a result, the extent of the lesion in which the spread and strength of lesion are evaluated at the same time can be divided and evaluated by a level.

In this way, the representative evaluation values of the image evaluation values are calculated from the image evaluation values for each of the plurality of sections that divide the region inside the captured organ using the information on the image-captured position inside the organ that is obtained by capturing each image, so the spread of the lesion can be evaluated accurately. The representative evaluation value is an indicator of the strength of lesion in the section. Therefore, it is possible to accurately evaluate not only the strength of lesion of the local biological tissue for each of the plurality of captured images, but also the comprehensive evaluation including the spread and strength of lesion in the depth direction of the organ. Here, the spread of the lesion indicates that the lesions are continuously spreading in the depth direction. Therefore, it is difficult to evaluate the spread of the lesion even if the image evaluation value is calculated by discretely capturing the images at several positions in the organ.

(Description of Electronic Endoscope System)

FIG. 1 is a block diagram illustrating a configuration of an electronic endoscope system 1 according to an embodiment of the present invention. As illustrated in FIG. 1, the electronic endoscope system 1 includes an electronic scope 100, a processor 200 for an electronic endoscope, a monitor 300, and a printer 400.

The processor 200 for an electronic endoscope includes a system controller 202 or a timing controller 206. The system controller 202 executes various programs stored in a memory 204 and controls the entire of the electronic endoscope system 1 in an integrated manner. Further, the system controller 202 changes various settings of the electronic endoscope system 1 according to an instruction by a user (surgeon or assistant) input to the operation panel 208. On the operation panel 208, for example, input for setting a statistic to be used as a representative value can be made, and at that time, different statistic can be set according to the assessment result to be described later. The timing controller 206 outputs a clock pulse for adjusting an operation timing of each part to each circuit in the electronic endoscope system 1.

The processor 200 for an electronic endoscope includes a light source unit 230 that supplies illumination light to the electronic scope 100. Although not illustrated, the light source unit 230 includes, for example, a high-intensity lamp, which emits white illumination light by receiving drive power from a lamp power source, such as a xenon lamp, a metal halide lamp, a mercury lamp, or a halogen lamp. The light source unit 230 is configured so that the illumination light emitted from the high-intensity lamp is condensed by a condensing lens (not illustrated) and then incident on an incident end of a light carrying bundle (LCB) 102 of the electronic scope 100 via a dimmer (not illustrated).

Alternatively, the light source unit 230 includes a plurality of light emitting diodes that emit light in a wavelength band of a predetermined color. The light source unit 230 is configured so that the light emitted from the light emitting diode is synthesized using an optical element such as a dichroic mirror, and the combined light is condensed as the illumination light by the condensing lens (not illustrated) and then is incident on the light carrying bundle (LCB) 102 of the electronic scope 100. A laser diode can also be used instead of the light emitting diode. The light emitting diode and the laser diode have features such as low power consumption and a low heat value as compared with other light sources, and therefore have a merit that a bright image can be acquired while suppressing the power consumption or the heat value. By acquiring the bright image, it is possible to improve the accuracy of the evaluation value related to inflammation, which will be described later.

Note that in the example illustrated in FIG. 1, the light source unit 230 is built in the processor 200 for an electronic endoscope, but may be provided in the electronic endoscope system 1 as a device separate from the processor 200 for an electronic endoscope. Further, the light source unit 230 may be provided at a distal end of the electronic scope 100 to be described later. In this case, the LCB 102 that guides the illumination light is unnecessary.

The illumination light incident on the LCB 102 from the incident end propagates in the LCB 102, is emitted from the end of the LCB 102 arranged in the distal end of the electronic scope 100, and is irradiated to the biological tissue inside the organ which is a subject via a light distribution lens 104. The reflected light from the biological tissue forms an optical image on a light receiving surface of a solid image sensor 108 via an objective lens 106.

The solid image sensor 108 is, for example, a single-plate color charge-coupled device (CCD) image sensor in which various filters of an infrared (IR) cut filter 108a and a Bayer array color filter 108b are arranged on the light receiving surface, and generates primary color signals of red (R), green (G), and blue (B) according to the optical image formed on the light receiving surface. Instead of the single-plate color CCD image sensor, a single-plate color complementary metal oxide semiconductor (CMOS) image sensor can also be used. The CMOS image sensor generally tends to have an overall darker image than the CCD image sensor. Therefore, in the quantization processing for evaluating the extent of the lesion to be described later, the advantageous effect of suppressing the fluctuation of levels of severity of the lesion of the lesion part due to the brightness of the image is more prominent in the case of using the CMOS image sensor. In this way, the electronic scope 100 captures an image of the biological tissue inside the organ using the solid image sensor 108 and generates the moving image.

A driver signal processing circuit 112 is provided inside a connection portion of the electronic scope 100 with the processor 200. The driver signal processing circuit 112 generates image signals (luminance signal Y and color difference signals Cb and Cr) by performing predetermined signal processing such as color interpolation and matrix calculation on the primary color signals input from the solid image sensor 108, and outputs the generated image signals to the image processing unit 220 of the processor 200 for an electronic endoscope. Further, the driver signal processing circuit 112 accesses the memory 114 and reads unique information of the electronic scope 100. The unique information of the electronic scope 100 recorded in the memory 114 includes, for example, the number of pixels or sensitivity of the solid image sensor 108, a frame rate that can be operated, a model number, and the like. The driver signal processing circuit 112 outputs the unique information read from the memory 114 to the system controller 202.

The system controller 202 performs various calculations based on the unique information of the electronic scope 100 and generates a control signal. The system controller 202 uses the generated control signal to control the operation or timing of each circuit in the processor 200 for an electronic endoscope so that processing suitable for the electronic scope 100 which is being connected to the processor 200 for an electronic endoscope are performed.

The timing controller 206 supplies a clock pulse to a driver signal processing circuit 112, an image processing unit 220, and a light source unit 230 according to the timing control by the system controller 202. The driver signal processing circuit 112 drives and controls the solid image sensor 108 at a timing synchronized with the frame rate of the image processed on the processor 200 for an electronic endoscope side according to the clock pulse supplied from the timing controller 206.

The image processing unit 220 is a unit that can perform image processing according to a surgeon's instruction or a preset processing content. Under the control of the system controller 202, the image processing unit 220 generates a video signal for displaying an endoscopic image or the like on a monitor based on the image signal of the captured image input from the driver signal processing circuit 112, and outputs the generated video signal to the monitor 300. In addition, the image processing unit 220 processes the plurality of captured images of biological tissue as part of image processing to evaluate an extent of a lesion of an organ, generates the video signal for displaying the evaluation result on the monitor, and outputs the generated video signal to the monitor 300. Specifically, the image processing unit 220 calculates the image evaluation value to be described later, which indicates the extent of the lesion of the biological tissue, from the plurality of images of the biological tissue obtained by the electronic scope 100. Note that the electronic scope 100 captures an image of the biological tissue inside the organ at the set frame rate while moving approximately continuously along the depth direction inside the organ (partially including the case where the image-captured position in the depth direction shifts in the opposite direction). Therefore, the image processing unit 220 uses the image evaluation values of images captured substantially continuously along the depth direction and the information on the image-captured position inside the organ that is obtained by capturing each of the plurality of images to calculate the representative evaluation values of the image evaluation values for each of the plurality of sections obtained by dividing the region inside the image-captured organ at a predetermined interval, and uses the representative evaluation value to evaluate the extent of the lesions which are continuously spreading in the depth direction inside the organ. The representative evaluation value is an evaluation value that represents the image evaluation values of the plurality of images captured in the section.

Further, the image processing unit 220 generates a color map image in which colors of each pixel in the image are replaced according to the pixel evaluation value to be described later. The image processing unit 220 generates information on the evaluation result of the extent of the lesion in the organ and a video signal for displaying the color map image on the monitor, and outputs the information and the video signal to the monitor 300. As a result, a surgeon can receive the evaluation of the extent of the lesion spreading in the depth direction of the organ of interest through the image displayed on the display screen of the monitor 300. The image processing unit 220 outputs the color map image and the information on the evaluation result of the extent of the lesion in the organ to the printer 400 as needed.

The processor 200 for an electronic endoscope is connected to a server 600 via a network interface card (NIC) 210 and a network 500. The processor 200 for an electronic endoscope can download information (for example, electronic medical chart information on a patient, information on a surgeon, and an evaluation result of an extent of a lesion in the same organ in the past) on an endoscopic examination from the server 600. The downloaded information is displayed, for example, on the display screen of the monitor 300 or the operation panel 208. In addition, the processor 200 for an electronic endoscope can upload the evaluation results of the endoscopic examination (endoscopic image data, examination conditions, evaluation result of the extent of the lesion of the organ, surgeon's opinion, and the like) to the server 600, and save the uploaded evaluation results in the server 600.

Figure 2:
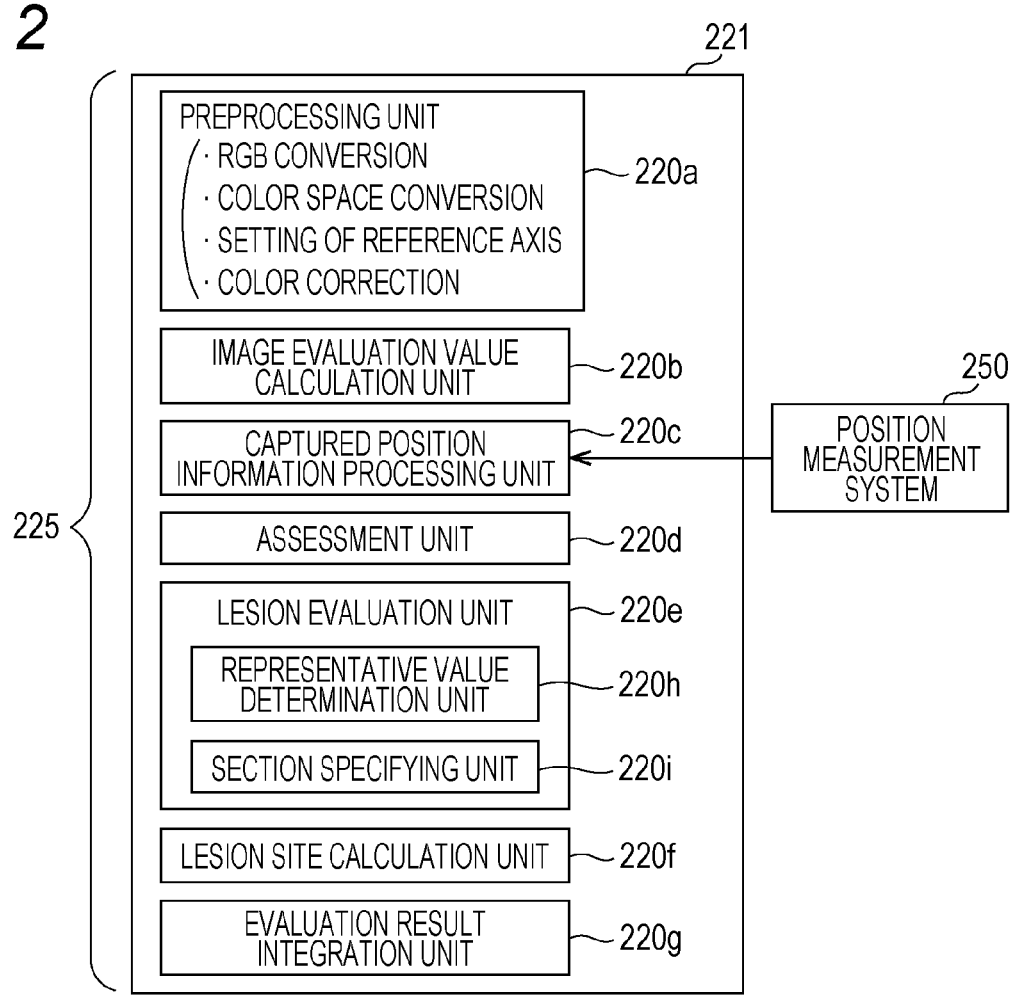
FIG. 2 is a diagram for explaining a configuration of a part of an image processing unit illustrated in FIG. 1 which evaluates a spread of a lesion in a depth direction of an organ.

FIG. 2 is a diagram illustrating a configuration of a part of the image processing unit 220 that evaluates the extent of the lesion in the section. The image processing unit 220 is a unit configured to process the plurality of images of the biological tissue captured by the electronic scope 100 and evaluate the extent of the lesion. The image processing unit 220 includes a preprocessing unit 220$a$, an image evaluation value calculation unit 220$b$, an image-captured position information processing unit 220$c$, an assessment unit 220$d$, a lesion evaluation unit 220$e$, a lesion site calculation unit 220$f$, and an evaluation result integration unit 220$g$. The preprocessing unit 220$a$, the image evaluation value calculation unit 220$b$, the image-captured position information processing unit 220$c$, the lesion evaluation unit 220$e$, the lesion site calculation unit 220$f$, and the evaluation result integration unit 220$g$ may be a software module formed by starting software stored in the memory 204, and may be configured by hardware.

Note that in the embodiment illustrated in FIG. 2, the electronic endoscope system 1 includes a position measurement system 250 to be described later, and the image processing unit 220 includes the image-captured position information processing unit 220$c$, but in another embodiment, the electronic endoscope system 1 does not include the position measurement system 250 and the image-captured position information processing unit 220$c$. Further, the image processing unit 220 includes the lesion site calculation unit 220$f$, but in another embodiment, does not include the lesion site calculation unit 220$f$.

According to an embodiment, the image evaluation value calculation unit 220$b$ evaluates the degree of inflammation, which is an example of lesion, for each image. Hereinafter, an example of the lesion including the inflammation that occurs in ulcerative colitis or the like will be described.

The image evaluation value calculation unit 220$b$ uses redness of biological tissue quantizing a degree of red color of the biological tissue for each pixel, as the pixel evaluation value, and integrates the pixel evaluation values of the entire image to calculate values combined into one numerical value as the image evaluation values. That is, the strength of the inflammation of the biological tissue is evaluated by using the degree of red color of the biological tissue. Hereinafter, a form for calculating the redness of biological tissue, which indicates the degree of inflammation, will be described as an example.

(Preprocessing Unit 220$a$)

The preprocessing unit 220$a$ is a unit that preprocesses an image for evaluating the degree of red color indicated by biological tissue. As illustrated as an example, the preprocessing unit 220$a$ performs each processing of RGB conversion, color space conversion, setting of a reference axis, and color correction.

The preprocessing unit 220$a$ converts the image signals (the luminance signal Y and the color difference signals Cb and Cr) input from the driver signal processing circuit 112 into the image color components (R, G, and B) using a predetermined matrix coefficient.

The preprocessing unit 220$a$ further performs color conversion to orthogonally project the image data converted into the image color component onto an RG plane. Specifically, the image color components of each pixel in an RGB color space defined by the three primary colors of RGB are converted into an image color component of RG. Conceptually, the image color components of each pixel in the RGB color space are plotted in the RG plane (for example, a partition in the RG plane on which the pixel value of the R component=0 to 255 and the pixel value of the G component=0 to 255 are taken). Hereinafter, for convenience of explanation, points of the image color components of each pixel in the RGB color space and points of the image color components plotted in the RG color space are referred to as "pixel correspondence points". The image color components of the RGB, respectively, of the RGB color space are, for example, color components having a wavelength of 620 to 750 nm, a wavelength of 495 to 570 nm, and a wavelength of 450 to 495 nm in order. Note that the color component constitutes a color space (including a color plane). Hue and saturation are excluded from the "color component".

The preprocessing unit 220a sets the reference axis in the RG plane needed to evaluate the redness of biological tissue.

In the biological tissue inside the organ of the patient as the subject, the R component of the image color components is dominant over other components (G component and B component) due to an influence of a hemoglobin pigment and the like. When the extent of the lesion of the lesion part is low and the lesion part is the inflammation part, the stronger the inflammation, the stronger the red color (R component) with respect to other colors (G component and B component). However, the color of the captured image in the organ changes depending on photographing conditions (for example, a lighting condition of the illumination light and a distance between the subject and the endoscope) that affect the brightness. Illustratively, a shaded portion that the illumination light does not reach is black (an achromatic color, for example, values of the image color components of R, G, and B are zero or a value approximating zero), and a portion where the illumination light is regularly reflected strongly is white (an achromatic color, for example, when the values of the image color components of R, G, and B is 8-bit gradation, the values are 255 or approximates 255). That is, even when the same inflammation part in which inflammation occurs is captured, the pixel value of the inflammation part increases as the illumination light hits strongly. Therefore, depending on the lighting condition of the illumination light, the value of the color component of the image may take a value that does not correlate with the strength of inflammation. Similarly, depending on the distance between the subject and the endoscope, the value of the color component of the image may take a value that does not correlate with the strength of inflammation.

In general, a healthy part inside the organ without the inflammation is covered with sufficient mucous membrane. On the other hand, the inflammation part inside the organ where inflammation is occurring is not covered with sufficient mucous membrane. Specifically, since the blood vessels dilate and blood and body fluids leak from the blood vessels, the mucous membrane becomes relatively thin and the color of the blood becomes easily visible. The mucous membrane is basically white, but the color is slightly yellowish, and the color (yellow) that appears on the image changes depending on the light and shade (thickness of the mucous membrane). Therefore, it is considered that the light and shade of mucous membrane is also one of the indicators for evaluating the degree of inflammation.

Figure 3:
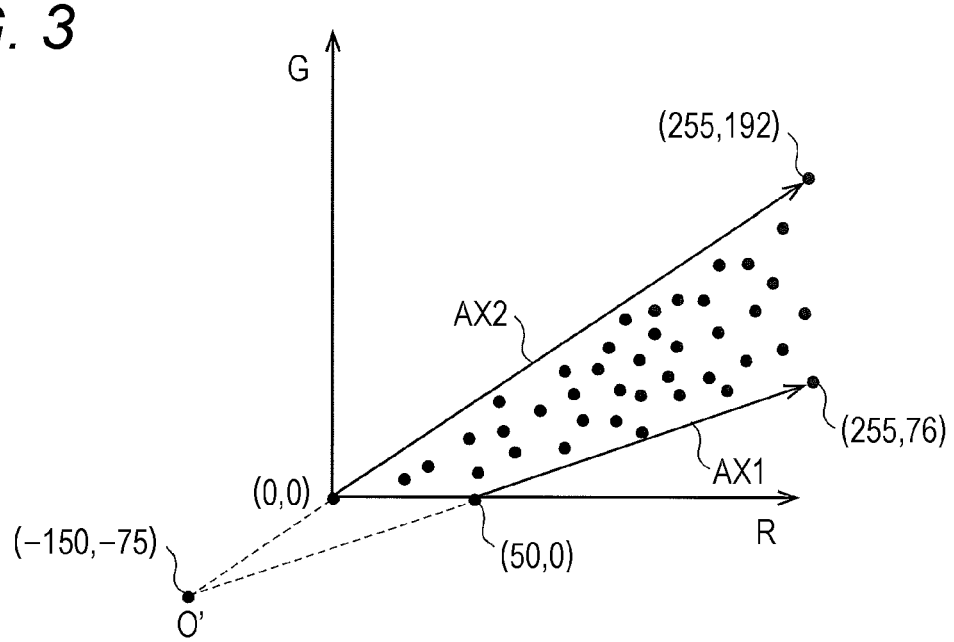
FIG. 3 is a diagram for explaining an example of a reference axis in a color space used in an embodiment.

Therefore, as illustrated in FIG. 3, a straight line passing through (50,0) and (255,76) is set as one of the reference axes in the RG color space, and a straight line passing through (0,0) and (255, 192) is set as one of the reference axes. For convenience of explanation, the former reference axis is referred to as "hemoglobin change axis AX1", and the latter reference axis is referred to as "mucous membrane change axis AX2". FIG. 3 is a diagram for explaining an example of the reference axis in the color space used in an embodiment.

The plot illustrated in FIG. 3 is a result of analyzing a large number of reference images inside the organ. The reference images used for the analysis include an inflammation image example at each stage such as an inflammation image example (an inflammation image example with the most severe level) with the highest degree of inflammation or an inflammation image example with the lowest degree of inflammation (substantially considered to be a healthy part). Note that in the example illustrated in FIG. 3, only a part of the plot obtained as the result of the analysis is illustrated for the sake of clarifying the drawing. The actual number of plots obtained as the result of the analysis is much larger than the number of plots illustrated in FIG. 3.

As described above, the stronger the inflammation, the stronger the R component of the color components of the image with respect to the other components (G component and B component). Therefore, in a boundary line between a region where the plot is distributed and a region where the plot is not distributed, an axis on the boundary line closer to the R axis than the G axis, in the example illustrated in FIG. 3, an axis on the boundary line passing through (50,0) and (255, 76) is set as an axis having a high correlation with a part having the strongest degree of inflammation, that is, a high correlation with a part having the highest degree of inflammation. This axis is the hemoglobin change axis AX1. The hemoglobin change axis AX1 is superposed with plots corresponding to the highest degree of inflammation captured under various photographing conditions, for example, various lighting conditions of illumination light. Therefore, the hemoglobin change axis AX1 is the axis on which the pixel correspondence points plotted converges as the degree of inflammation of the biological tissue increases.

On the other hand, the closer to the healthy part, the stronger the G component (or B component) of the color components of the image with respect to the R component. Therefore, in the boundary line between the region where the plot is distributed and the region where the plot is not distributed, an axis on the boundary line closer to the G axis than the R axis, in the example illustrated in FIG. 3, an axis on the boundary line passing through (0.0) and (255,192) is a part having the lowest degree of inflammation, that is, a part having the lowest degree of inflammation, and is set as an axis having a high correlation with one substantially considered to be the healthy part. This axis is the mucous membrane change axis AX2. The mucous membrane change axis AX2 is superposed with plots corresponding to the lowest degree of inflammation captured under various photographing conditions, for example, various lighting conditions of illumination light, that is, one substantially considered to be the normal part Therefore, the mucous membrane change axis AX2 is the axis on which the pixel correspondence points to be plotted converge as the degree of inflammation decreases (the closer to the healthy part).

In addition, the highest part of the extent of the lesion in the lesion part is accompanied by bleeding. On the other hand, the lowest part of the extent of the lesion is a substantially normal healthy part, and therefore is covered with a sufficient mucous membrane. Therefore, the plot in the RG color space illustrated in FIG. 3 can be considered to be distributed in the region sandwiched between the axis most correlated with blood (hemoglobin pigment) and the axis most correlated with the color of the mucous membrane. Therefore, of the boundary lines between the region where the plot is distributed and the region where the plot is not distributed, the boundary line closer (stronger R component) to the R axis corresponds to the axis (hemoglobin change axis AX1) showing the inflammation part with the highest degree of inflammation, and the boundary line closer (stronger G component) to the G axis corresponds to the axis (mucous membrane change axis AX2) showing the inflammation part with the lowest degree of inflammation.

After setting the reference axis in this way, the processing of calculating the redness of biological tissue indicating the degree of red color, which will be described later, is performed on the color component of the image orthogonally projected. Before the processing of calculating the redness of biological tissue, the color correction is performed on the pixel data orthogonally projected.

The reference axis illustrated in FIG. 3 is an example, and the reference axis varies depending on a type of disease.

The preprocessing unit 220a performs the color correction on the color components of the image represented in the RG color space before calculating the inflammation evaluation value. The correction matrix coefficient is saved in the memory 204. Despite the same inflammation part, to prevent the inflammation evaluation value to be described later from varying when captured by different electronic endoscope systems (in other words, to suppress inter-individual error in the electronic scope), the preprocessing unit 220a corrects pixel data (R, G), which is the pixel corresponding points in the RG color space of each pixel, as illustrated in the following equation using the correction matrix coefficient.

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Corrected pixel data (R component)
$G_{new}$: Corrected pixel data (G component)
$M_{00}$ to $M_{11}$: Correction matrix coefficient
R: Pixel data before correction (R component)
G: Pixel data before correction (G component)
(Image Evaluation Value Calculation Unit 220b)

Figure 4:
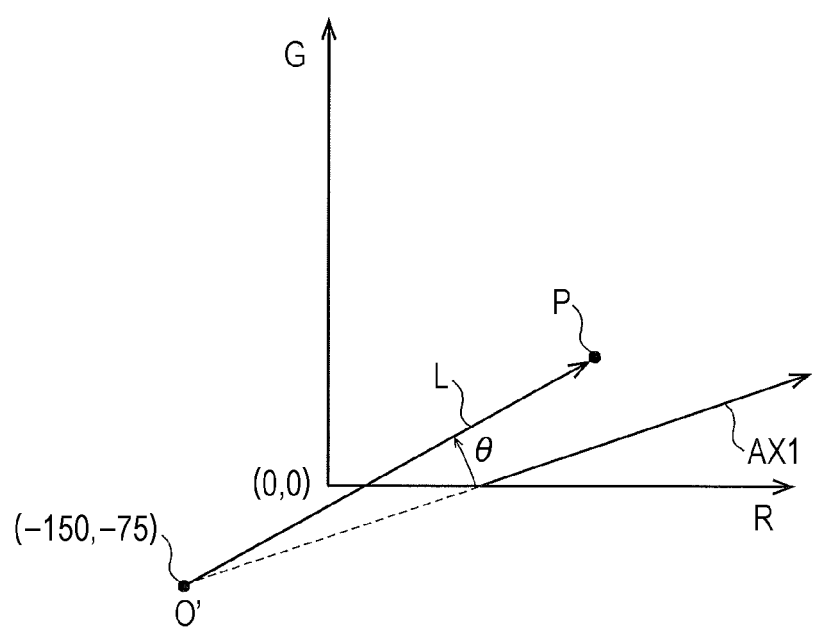
FIG. 4 is a diagram for explaining a method of calculating a deviation angle for calculating redness of biological tissue used in an embodiment.

The image evaluation value calculation unit 220b selects one pixel of interest from the pixels and calculates a deviation angle for calculating the degree of inflammation for the selected pixel of interest based on the information on the color component of the pixel of interest. That is, the quantification process is performed to quantify the degree of red color of the biological tissue based on the information on the color component of the pixel. FIG. 4 is a diagram for explaining a method of calculating a deviation angle for calculating redness of biological tissue used in an embodiment. Specifically, as illustrated in FIG. 4, the image evaluation value calculation unit 220b sets an intersection of the hemoglobin change axis AX1 and the mucous membrane change axis AX2 as a reference point O', and calculates the deviation angle θ in which a direction of a line segment L connecting the reference point O' and the pixel corresponding point P of the pixel of interest deviates from the reference axis AX1. Note that the reference point O' is located at coordinates (−150, −75). The example in which the reference point O' is set to the coordinates (−150, −75), but is not limited thereto. The reference point O' can change as appropriate, and may be, for example, the intersection of the R axis and the G axis in the RG color space.

An appropriate coordinate position as the reference point O' is, for example, a position where the error of the evaluation result due to the fluctuation of the brightness can be reduced. Specifically, the reference point O' is preferably set in advance a point where the error between the evaluation result in a dark part (brightness is less than the predetermined value) and the evaluation result in a non-dark part (brightness is equal to or greater than the predetermined value) is minimized.

Also, for example, if the reference point O' is set between coordinates (−10, −10) and (10,10), compared with the case where the coordinates (−150, −75) and the like are set as the reference point O', the amount of change in the angle θ in the case where the pixel correspondence point changes is larger, so the resolution is improved. As a result, the highly accurate evaluation result can be obtained.

On the other hand, by setting the reference point O' between the coordinates (−50, −50) and (−200, −200), the evaluation result indicating the degree of inflammation is less affected by noise.

When the brightness of the photographed image of the biological tissue inside the organ changes depending on the lighting condition of the white light, the color of the image is affected by individual differences, a photographing location, a state of inflammation, and the like, but in the RG color space, generally, the inflammation part with the highest level of severity changes along the hemoglobin change axis AX1, and the inflammation part with the lowest degree of inflammation changes along the mucous membrane change axis AX2. In addition, it is estimated that the color of the image of the inflammation part with the intermediate degree of inflammation changes with the same tendency. That is, when the pixel corresponding point corresponding to the inflammation part changes by the lighting condition of the illumination light, the pixel corresponding point shifts in an azimuth direction starting from the reference point O'. In other words, when the pixel corresponding point corresponding to the inflammation part changes by the lighting condition of the illumination light, the deviation angle θ with respect to the mucous membrane change axis AX2 moves constantly, and the distance from the reference point O' changes. This means that the deviation angle θ is a parameter that is substantially unaffected by the change in the brightness of the image.

The smaller the deviation angle θ, the stronger the R component with respect to the G component, which indicates that the degree of red color in the lesion part is relatively large. In addition, the larger the deviation angle θ, the stronger the G component with respect to the R component, which indicates that the degree of red color is relatively small. Therefore, the image evaluation value calculation unit 220b normalizes the angle θ so that the value becomes 255 when the deviation angle θ is zero and the value becomes zero when the deviation angle θ is $θ_{MAX}$. Note that $θ_{MAX}$ is equal to the angle formed by the hemoglobin change axis AX1 and the mucous membrane change axis AX2. That is, the image evaluation value calculation unit 220b sets the value in the range of 0 to 255 obtained by normalizing the deviation angle θ calculated based on the information of the color component of each pixel of interest for each pixel of interest to the redness of biological tissue (pixel evaluation value).

Note that the pixel of interest is selected one by one for all the pixels of the image.

Note that in the example illustrated in FIG. 4, the RG color space is used as the color space, but the RB color space can be used instead of the RG color space.

The image evaluation value calculation unit 220b calculates the redness of biological tissue, which is a normalized value of the deviation angle θ, as the pixel evaluation value, but in some cases, the whiteness of biological tissue, which indicates the degree of feature of the ulcer of the biological tissue, can also be calculated as an evaluation value. For example, a gain adjustment that assigns a linear gain to the pixel value of each color component of each pixel of biological tissue image is performed, and tone enhancement processing that substantially widens a dynamic range near a color gamut peculiar to lesion to increase an effective resolution of color representation, and thus, an ulcer part containing white moss and purulent mucus of ulcerative colitis indicates white and the inflammation part showing red color containing edema and easy bleeding or the normal part showing yellow or green color can be distinguished by the color component. As illustrated in FIG. 4, the whiteness of biological tissue can be calculated using the deviation angle with respect to a reference axis different from the reference axis AX, which is displayed on the color space that is the coordinate axis of the two color components (two of the R, G, and B components) or the three color components (the R, G, and B components). Note that the tone enhancement processing is performed by the preprocessing unit 220a.

The image evaluation value calculation unit 220b calculates one image evaluation value using the pixel evaluation value of each pixel. For example, in the captured image, the pixels representing the image of the biological tissue to be evaluated are selected, and the integrated value or the average value of the pixel evaluation values of the selected pixels is calculated as one image evaluation value. Alternatively, for example, by extracting the pixels to be evaluated based on the color component or the brightness component in a predetermined range from the RGB color component for each pixel or the brightness component of the pixel and obtaining the average value of the pixel evaluation values of the extracted pixels, obtaining a weighted average value using a predetermined weighting coefficient, or performing integration processing, the image evaluation value calculation unit 220b calculates one image evaluation value. It is preferable that the pixel portion to be evaluated in the image is a portion having a value of a color component within a predetermined range assumed in the biological tissue in order to evaluate the degree of inflammation of the organ with high accuracy, and is a pixel portion having the brightness component equal to or greater than the predetermined value illuminated by the illumination light.

The image evaluation value calculated by the image evaluation value calculation unit 220b is transmitted to the assessment unit 220d and the lesion evaluation unit 220e.

The image evaluation value calculation unit 220b further creates a color map image in which the image of the biological tissue is mosaicked with a display color that changes according to the redness of biological tissue. A table in which the pixel evaluation value and the predetermined display color are associated with each other is stored in a storage area of the memory 204 in order to create the color map image. In the above table, for example, different display colors are associated with each value in increments of 5. Illustratively, blue is associated in the range where the pixel evaluation value is 0 to 5, different display colors are associated according to the order of colors in a color circle every time the pixel evaluation value increases by 5, and red is associated in the range where the pixel evaluation value is 250 to 255. The display color is a color that approaches a warm color from a cold color, for example, from blue to yellow to red as the redness of biological tissue is larger. The image evaluation value calculation unit 220b determines the display color of the selected pixel of interest on the color map image according to the redness of biological tissue of the pixel of interest based on the above table.

In this way, the image evaluation value calculation unit 220b creates a color map image in which colors are assigned according to the redness of biological tissue.

(Image-Captured Position Information Processing Unit 220c)

The image-captured position information processing unit 220c acquires the information on the image-captured position transmitted from the position measurement system 250 provided in the electronic endoscope system 1, and associates the acquired position information with the captured image. The position measurement system 250 is a system that uses a sensor to acquire, for example, the position of the solid image sensor 108 located at the distal end of the electronic scope 100 inserted into the organ, and furthermore each position of subsequent flexible tubes, a system that acquires an insertion length of the inserted electronic scope 100 from the opening end of the organ, or a system that allows a surgeon who sees the captured image displayed on the monitor 300 to acquire a specific part passing signal indicating that the distal end of the inserted electronic scope 100 passes through a feature part in the organ.

The acquired information on the image-captured position is sequentially transmitted to the assessment unit 220d and the lesion evaluation unit 220e.

In a system that acquires the position of the solid image sensor 108 using the sensor, for example, a plurality of magnetic sensors are provided in the position near the solid image sensor 108 of the distal end of the electronic scope 100 and in the flexible tube subsequent to the side of the processor 200 from the distal end at a predetermined interval, and the electronic scope 100 can apply a magnetic field with different strength depending on the position from the outside of the human body inserted into the organ, know the position of the magnetic sensor provided at the distal end by measuring the strength of the magnetic field with the magnetic sensor, and furthermore, and know the curved shape of the flexible tube in the organ from the positions of the plurality of magnetic sensors. As a result, it is possible to know the position of the distal end of the solid image sensor 108, the shape of the electronic scope 100 in the organ, and furthermore, the insertion length of the electronic scope 100 from the opening end of the organ.

In the case of the system that acquires the insertion length of the electronic scope 100 inserted from the opening end of the organ, for example, by acquiring the extent to which the biological tissue moves between images with an adjacent capture time in the captured moving image using optical flow processing and by integrating the acquisition results to calculate the moving distance, it is possible to acquire the information on the insertion length of the current electronic scope 100. Further, for example, by measuring the extended length of the flexible tube following from the distal end of the inserted electronic scope 100 into the organ, it is possible to acquire the information on the insertion length of the current electronic scope 100.

In the system that acquires the specific part passing signal of the organ, by pressing a button with a surgeon's hand when the identifiable specific part inside the organ appears in the image and passes therethrough while the surgeon is looking at the image displayed on the monitor 300, it is possible to generate the specific part passing signal and for the image-captured position information processing unit

220c to acquire the specific part passing signal. The position of the specific part inside the organ includes, for example, a position where an ascending colon begins, a position where the ascending colon ends, the large intestine is bent, and a transverse colon begins, a position where the transverse colon ends, the large intestine is bent, and the descending colon begins, a position where the descending colon ends, the large intestine is bent, and a sigmoid colon begins, a position where the sigmoid colon ends and a rectum begins, and a position where the rectum ends and reaches an anus, when the organ is the large intestine.

(Assessment Unit 220d)

The assessment unit 220d is configured to assess whether the extent of the lesion is changed in the section based on the degree of variation of the image evaluation values of the plurality of images captured in the section. By performing such an assessment, it is possible to obtain an indicator (representative evaluation value) that more appropriately indicates the extent of the lesion in the section and accurately evaluate the extent of the lesion. The variation in the evaluation value may be the variation in the image evaluation value of all the images captured in the section, or may be the variation in the image evaluation value of some images as described later. In addition, examples of the section where the extent of the lesion is changed include a section where a plurality of the extent of the lesions are present and a section where both the lesion part and normal part are present. Examples of the plurality of extent of lesions include a plurality of ranks or a plurality of levels, which will be described later, which are different from each other According to an embodiment, it is preferable that the assessment unit 220d is configured to perform an assessment using an indicator indicating the degree of variation obtained from the image evaluation value, and perform an assessment if the extent of the lesion is changed in the section when the degree of variation indicated by this indicator is equal to or greater than a preset threshold value (predetermined value). Examples of the indicator include the following indicators 1 to 4.

Indicator 1: Difference between the maximum values and minimum values of the image evaluation value (the size of the range of the image evaluation value)

Indicator 2: Standard deviation (or variance) of the image evaluation value Indicator 3: An indicator indicating the degree of fit of the regression line in which the image evaluation values are regressed in the order of the captured images.

Indicator 4: An inclination of the regression line in which image evaluation values are regressed to the image-captured position.

The assessment performed using indicators 1 to 4 will be described with reference to FIGS. 5 to 8.

FIGS. 5 to 8 illustrate graphs showing the relationship between the number of measurements (the number of captures) and the image evaluation value of the captured image in each section for two sections, and (a) of FIGS. 5 to 8 illustrates a graph in the section where the variation in the image evaluation value is small and (b) of FIGS. 5 to 8 illustrates a graph in the section where the variation in the image evaluation value is large.

Figure 5:
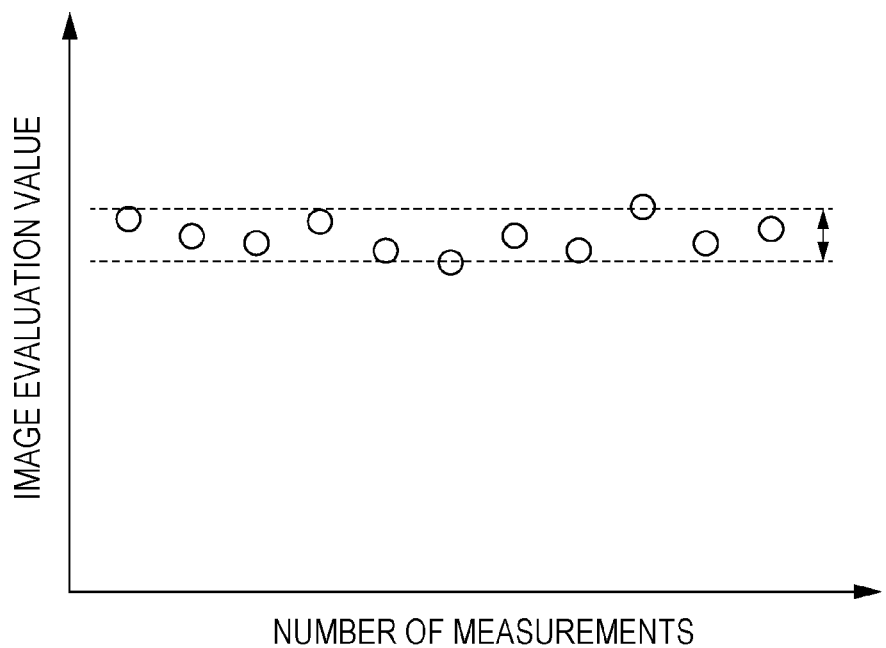
FIGS. 5(a) and 5(b) are graphs illustrating a relationship between the number of captures and an image evaluation value of a captured image.
Figure 5:
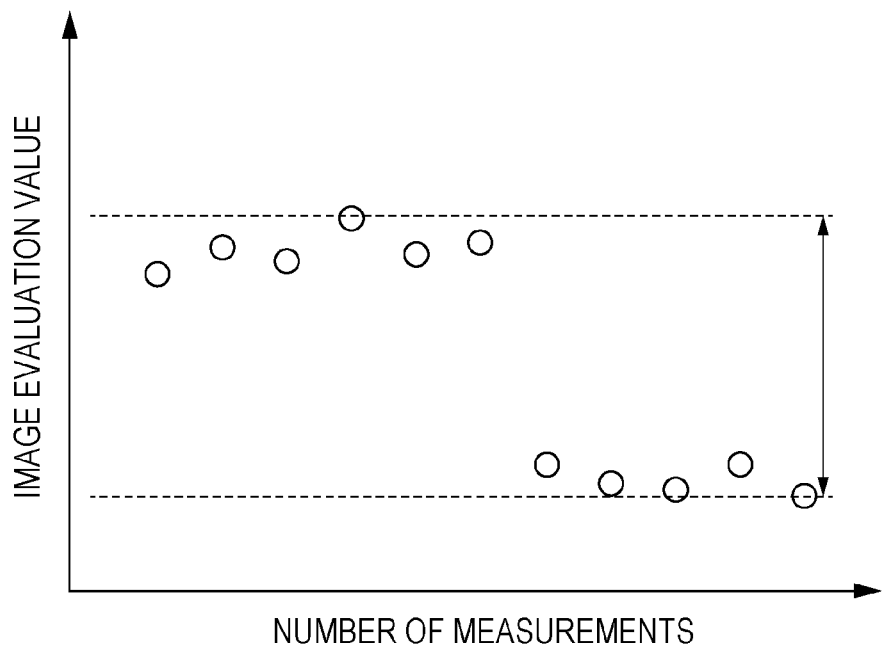
Figure 6:
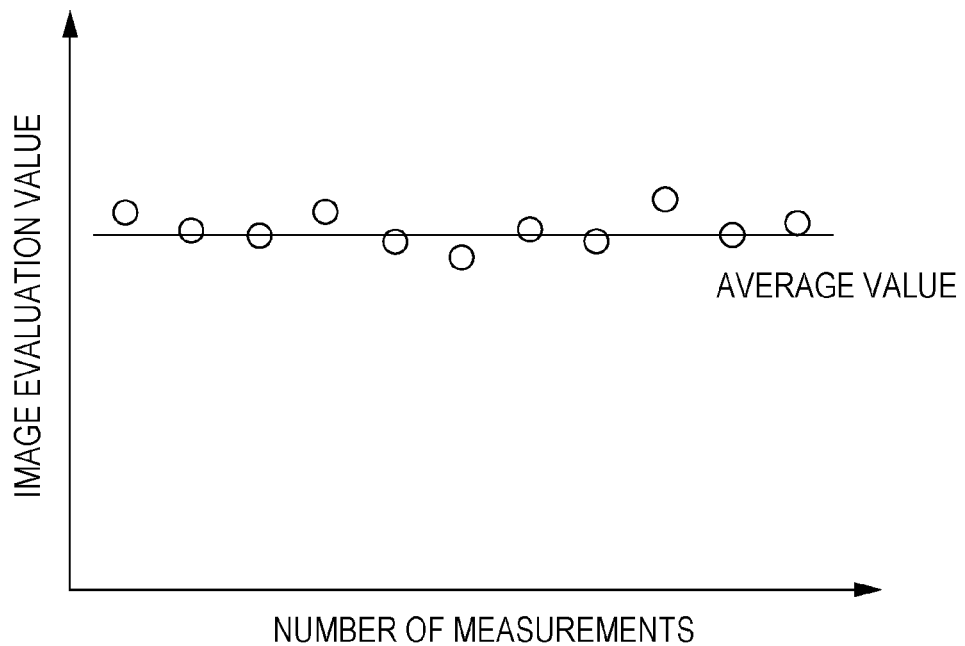
FIGS. 6(a) and 6(b) are graphs illustrating the relationship between the number of captures and the image evaluation value of the captured image.
Figure 6:
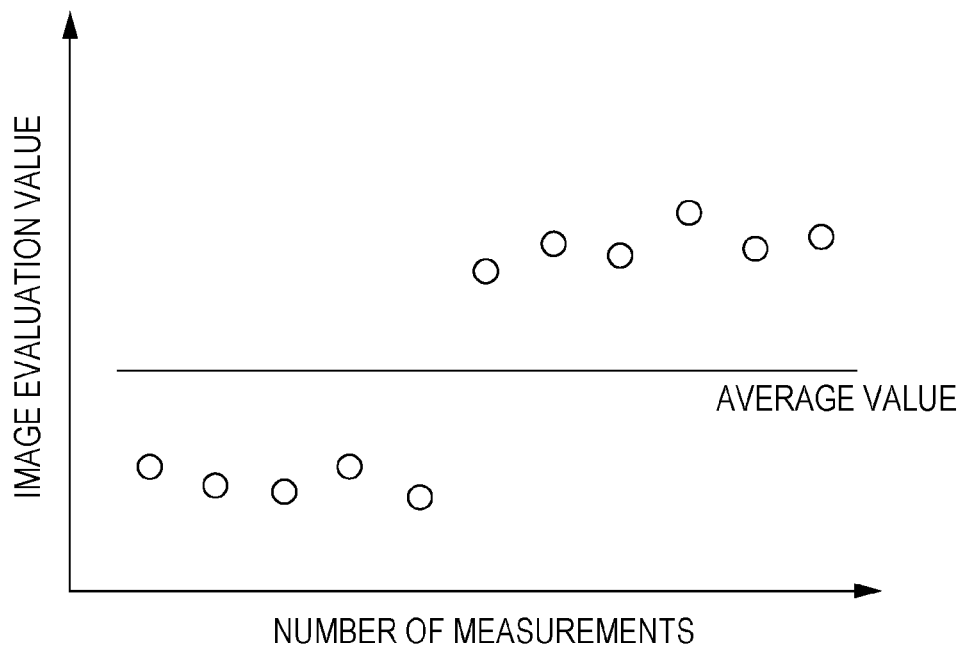
Figure 7:
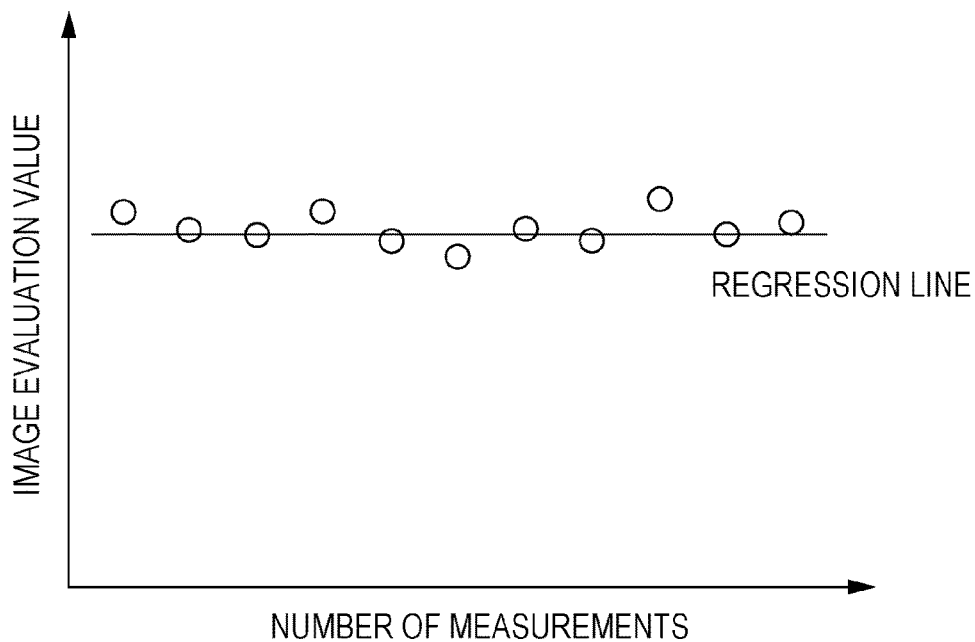
FIGS. 7(a) and 7(b) are graphs illustrating the relationship between the number of captures and the image evaluation value of the captured image.
Figure 7:
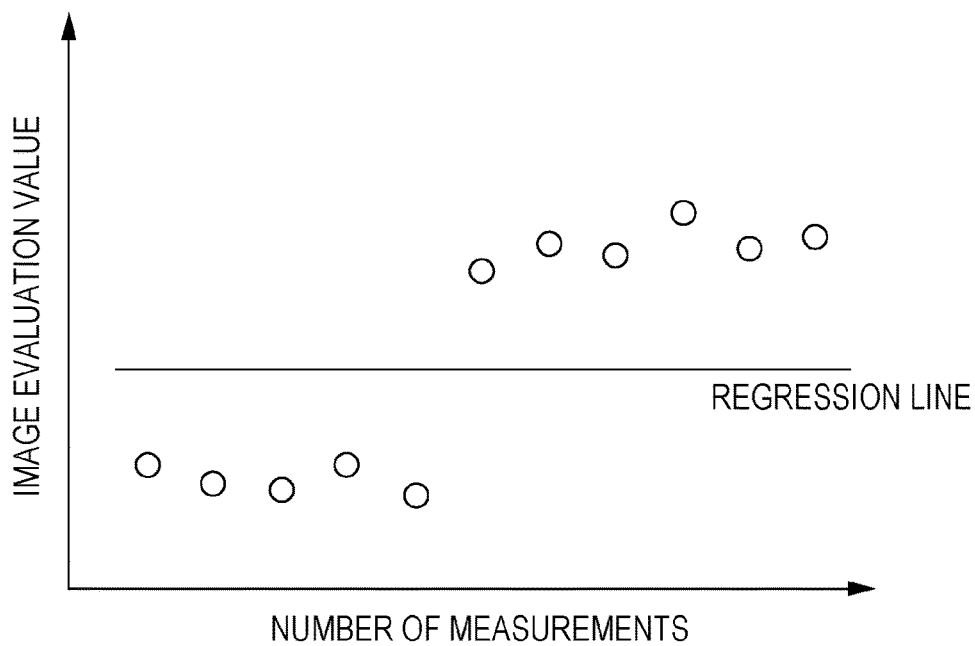
Figure 8:
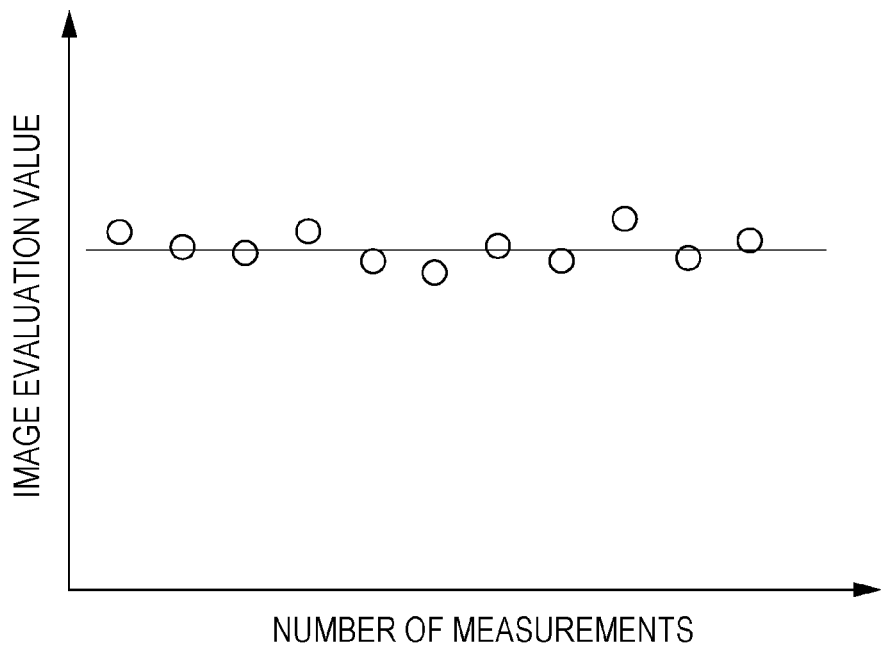
FIGS. 8(a) and 8(b) are graphs illustrating the relationship between the number of captures and the image evaluation value of the captured image.
Figure 8:
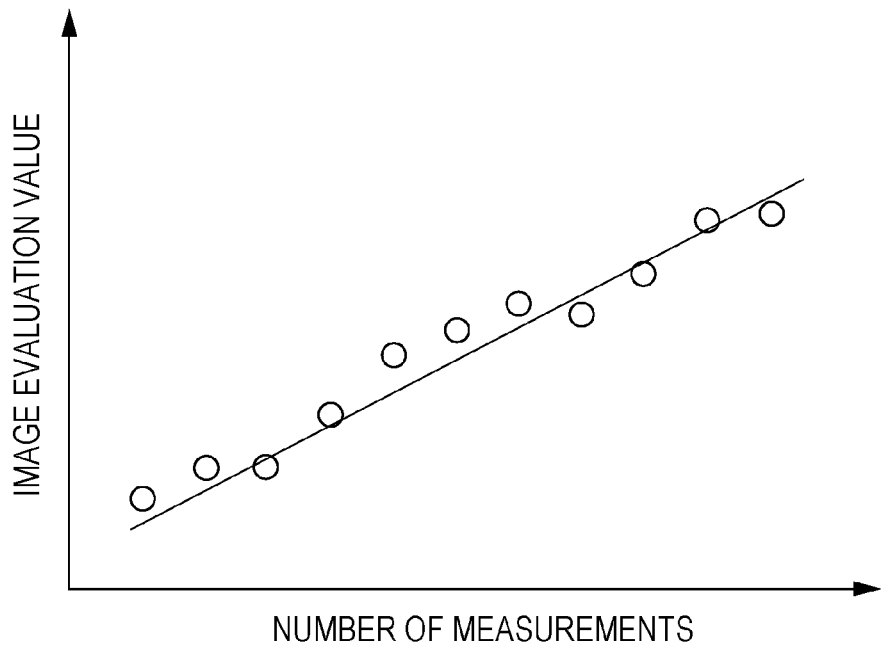

In FIGS. 5 to 7, the number of measurements (the number of captures) on the horizontal axis indicates that the plot located on the right side is captured later, and is arranged from the right to the left in the order of the capture. In FIG. 8, the horizontal axis indicates the image-captured position along the depth direction in the organ, and the plot located on the right side indicates that the plot is captured on the opening end side of the organ.

When performing the assessment using the indicator 1, by setting in advance the threshold value distinguishing the degree of variation of the image evaluation value between FIGS. 5(a) and 5(b) with respect to the difference between the maximum values and minimum values of the image evaluation value, as illustrated in FIG. 5(b), when the difference between the maximum value and the minimum value is equal to or greater than the threshold value, it is possible to perform the assessment when the strength of lesion is changed in the section. In addition, as illustrated in FIG. 5(a), when the difference between the maximum value and the minimum value is less than the threshold value, it can be assessed that the strength of lesion is not changed in the section.

When performing the assessment using the indicator 2, by setting in advance the threshold value distinguishing the degree of variation of the image evaluation value between FIGS. 6(a) and 6(b) with respect to the standard deviation (or variance), as illustrated in FIG. 6(b), when the standard deviation (or variance) is equal to or greater than the threshold value, it is possible to perform the assessment when the strength of lesion is changed in the section. In addition, as illustrated in FIG. 6(a), when the difference between the standard deviation (or variance) is less than the threshold value, it can be assessed that the strength of lesion is not changed in the section. In addition, FIGS. 6(a) and 6(b) illustrate the average value of the image evaluation values used for the calculation of the standard deviation (or variance).

As for the threshold values for the indicators 1 and 2, specifically, the degree of variation of the image evaluation value caused by the change in the brightness of the image is less than the threshold value, and the degree of variation of the image evaluation value caused by the change in the extent of the lesion in the section is set to be equal to or greater than the threshold value.

When performing an assessment using the indicator 3, by setting in advance the threshold value for distinguishing the degree of variation of the image evaluation value with respect to the regression line between FIGS. 7(a) and 7(b) with respect to the degree of fit of the regression line, as illustrated in FIG. 7(b), if the indicator indicating the degree of fit exceeds the threshold value and indicates a good fit, it can be assessed that the strength of lesion is changed in the section. In addition, as illustrated in FIG. 7(a), if the indicator indicating the degree of fit is equal to or less than the threshold value and indicates a bad fit, it can be assessed that the strength of lesion is not changed in the section.

The regression line illustrated in FIG. 7 is a straight line obtained by using the least squares method. Further, for the indicator 3, that is, the indicator indicating the degree of fit of the regression line, for example, a determination coefficient $R^2$ represented by the following formula is used.

$$R^2 = \frac{\sum_{i=1}^{n}(y_i - y'_i)^2}{\sum_{i=1}^{n}(y_i - Y)^2}$$

$y_i$: Image evaluation value of the captured image
$y'_i$: Image evaluation value on the regression line
$Y$: Average value of image evaluation value of the captured image
$n$: The number of captured images The determination coefficient is indicated by a value from 0 to 1, and as the determination coefficient approaches to 1, it indicates that the fit of the regression line is good. The threshold value is set to a value between 0 and 1. As a result, when the determination coefficient exceeds a preset threshold value, it is assessed that the strength of lesion is changed in the section. In addition, when the determination coefficient is equal to or less than the threshold value, it is assessed that the strength of lesion is not changed in the section. According to an embodiment, it is also preferable to use a correlation coefficient R indicating the correlation between the image evaluation value of the captured image and the image evaluation value on the regression line as the indicator 3 instead of the determination coefficient.

As described above, the electronic endoscope system 1 does not have to include the position measurement system 250 and the image-captured position information processing unit 220c. In this case, in the graphs illustrated in FIGS. 5 to 7, there is no correlation between the image evaluation value and the image-captured position, but it can be assessed whether the extent of the lesion is changed within the section using the above indicators 1 to 3. On the other hand, for example, even when it is indicated that the regression line fits well, the variation in the image evaluation value may be large as illustrated in FIG. 8(b). In this case, since it should be assessed that the extent of the lesion is changed in the section, it is preferable to perform the assessment using the above indicator 4. That is, according to an embodiment, it is preferable that the assessment unit 220d may be configured to perform the assessment using the inclination of the regression line in which the image evaluation values are regressed in the order of the image-captured positions along the depth direction, and perform the assessment if the extent of the lesion is changed in the section when the inclination is equal to or greater than a predetermined value. In this case, it is preferable that the assessment unit 220d is configured to perform the assessment using the inclination of the regression line when the indicator indicating the degree of fit exceeds the threshold value. As a result, not only when the indicator indicating the degree of fit of the regression line exceeds the threshold value, but also when the indicator indicating the degree of fit of the regression line is equal to or less than the threshold value (when the fit is good), if the inclination of the regression line is large, it can be assessed that the extent of the lesion is changed. On the other hand, when the indicator indicating the degree of fit of the regression line is equal to or less than the threshold value, it can be assessed that the extent of the lesion is not changed when the inclination of the regression line is small. Such an assessment using the indicator 4 can be performed when the electronic endoscope system 1 includes the image-captured position information processing unit 220c and the position measurement system 250.

When performing the assessment using the indicator 4, by setting in advance the threshold value distinguishing the degree of variation of the image evaluation value between FIGS. 8(a) and 8(b) with respect to the inclination of the regression line, as illustrated in FIG. 8(b), when the inclination of the regression line is equal to or greater than the threshold value, it is possible to perform the assessment when the strength of lesion is changed in the section. In addition, as illustrated in FIG. 8(a), when the inclination of the regression line is less than the threshold value, it can be assessed that the strength of lesion is not changed in the section. Also, when the assessment is performed using the indicator 4, it is possible to understand how the strength of lesion is changed and the degree of the change. For example, it can be seen whether the strength of lesion is changed suddenly or slowly.

When the electronic endoscope system 1 includes the position measurement system 250 and the image-captured position information processing unit 220c, according to an embodiment, the assessment unit 220d further uses the information on the image-captured position to specify the region in the section where the extent of the lesion is changed. By specifying the region where the strength of lesion is changed, it can be seen that the region where the extent of the lesion is changed exists in, for example, a spot shape, or whether the region where the extent of the lesion is changed continuously exists to be connected to lesion parts of adjacent sections, and the like. The spot-like region may exist in various lengths in the depth direction depending on the length of the section. For example, one or more spot-like regions may exist within one section, or two or three spot-like regions may exist continuously across two or three or more sections. In addition, there may be a plurality of lesion parts that exist continuously so as to be connected to the lesion part of the adjacent section in one section. That is, there may be two lesion parts in one section that are each connected to the lesion parts of the sections on both sides of the section. In addition, as an example of the region where the extent of the lesion is changed, the region in one lesion part that continuously extends in the depth direction or there is a region in the section including the boundary between the lesion part and the normal part (start position or end position described later).

Also, according to an embodiment, it is preferable that the assessment unit 220d further uses the information on the image-captured position to specify the degree of change in the strength of lesion with respect to the region in the section where the extent of the lesion is changed. For example, depending on whether the degree of change (inclination) in the strength of lesion is greater than or equal to a preset threshold value or less than a preset threshold value, it can be determined whether the change in the strength of lesion is sudden or slow. Further, it can be seen from the direction of change in the strength of lesion along one direction of the depth direction whether the strength of lesion is stronger or weaker in the one direction. That is, according to an embodiment, it is preferable that the assessment unit 220d may be configured to specify the degree of change in the lesion in the section according to the size in the inclination of the regression line.

In an embodiment, these specification made by the assessment unit 220d may be configured to be made by the lesion site calculation unit 220f.

According to an embodiment, the assessment unit 220d is preferably configured to perform the assessment based on the variation in the evaluation value of a part of the evaluation values. For example, when water for cleaning, blood, stool, and the like adheres to the site of the biological tissue to be captured or the distal end of the endoscope, the image evaluation value that deviates significantly from the average value of the image evaluation values of all captured images may be calculated. If the assessment of whether the extent of the lesion is changed in the section is performed based on the variation of the image evaluation value including such outliers, the accuracy of the assessment is lowered. In this embodiment, by performing the assessment based on the variation in the remaining image evaluation values excluding the outliers as some of the image evaluation values, it is possible to increase the accuracy of the assessment on whether the strength of the lesion is changed in the section and obtain the indicator (representative evaluation value) appropriately indicating the extent of the lesion in the section. As a result, the extension of lesion can be evaluated with high accuracy.

Examples of a method of excluding outliers may include a method of excluding image evaluation values within a certain percentage (for example, a few percent) of the range (the difference between a maximum value and a minimum value) of variation in the image evaluation value from the maximum value, the minimum value, or both the maximum value and the minimum value of the image evaluation values of all the images captured in the section. Further, examples of a method of excluding outliers may include a method of excluding an inflammation evaluation value outside a predetermined range of inflammation evaluation value among the inflammation evaluation values of all the images captured in the section. Examples of another method of excluding outliers may include excluding outliers detected by a test from the image evaluation values of all the images captured in the section, detecting the other outliers by performing a test again, and repeating the exclusion. According to an embodiment, the outliers are preferably excluded, as the target, from the image evaluation value obtained when all the images are captured in the region in the organ to be captured or a predetermined segment, and according to another embodiment, the image can be excluded while being reproduced.

(Lesion Evaluation Unit 220e)

The lesion evaluation unit 220e uses the information on the image-captured position transmitted from the image-captured position information processing unit 220c to calculate the representative evaluation value of the image evaluation value from the image evaluation values of the plurality of images of the biological tissue captured within the plurality of sections, respectively, for each of the plurality of sections obtained by dividing the region inside the image-captured organ at the predetermined interval. Furthermore, the lesion evaluation unit 220e evaluates the spread of the lesions that are continuously spreading in the depth direction inside the organ by using the representative evaluation value. For example, in the case of ulcerative colitis in a large intestine, it can be evaluated that the lesion is spreading from the rectum to the descending colon. In such an evaluation, the spread of the lesion can be evaluated assuming that the region in which the representative evaluation value exceeds a preset threshold value is the lesion part.

Here, the section may be one defined in advance by the surgeon, or the section may be divided by the specific part passing signal. When a section is defined by the specific part passing signal, the section is called a segment.

This segment is a part that can be identifiably distinguished from other parts in one organ, for example, when the organ is a large intestine, the organ includes a segment of ascending colon, a segment of transverse colon, a segment of descending colon, a segment of sigmoid colon, a segment of rectum, and the like. In such segments, the section is divided by the specific part passing signal.

The lesion evaluation unit 220e has the representative value determination unit 220h. The representative value determination unit 220h is configured to define the representative evaluation value in a different method when the assessment unit 220d assesses that the strength of lesion is changed in the section and when the assessment unit 220d assesses that the strength of lesion is not changed in the section. As described above, the brightness of the image changes depending on the photographing conditions such as the distance between the subject and the endoscope. Therefore, even if a site of biological tissue having the same strength of inflammation is captured, the image evaluation value fluctuates and variations occur. On the other hand, image evaluation value also fluctuates even when the extent of the lesion is changed along the depth direction in the organ, and variations occur. Therefore, if, for example, the average value of the image evaluation value is used as the representative evaluation value, the average value of the image evaluation value becomes the representative evaluation value showing the average strength of inflammation not only when the image evaluation value varies due to the brightness of the image, but also when the image evaluation value varies due to the change in the strength of inflammation. As a result, it becomes difficult to understand that there is the lesion part in the section that indicates a stronger strength of inflammation than the representative evaluation value indicates, and therefore the strength of inflammation cannot be determined appropriately. It is important to know the strength of lesion in considering treatment methods for the lesion part. Therefore, as described above, the representative value determination unit 220h defines the representative evaluation value in a different method when the extent of the lesion is assessed to be changed and when the extent of the lesion is assessed not to be changed. As a result, the indicator that appropriately indicates the extent of the lesion in the section can be obtained, and the evaluation of the extent of the lesion can be performed accurately.

According to an embodiment, the method is preferably a statistical method.

Specifically, according to an embodiment, when the strength of lesion is assessed to be changed in the section, the representative value determination unit 220h is preferably configured so that the maximum value of the image evaluation values of at least some of the plurality of images captured in the section is the representative value of the section. As a result, it is possible to optimally indicate the extent of the lesion for the section where the extent of the lesion is changed.

In addition, according to an embodiment, when the strength of lesion is assessed not to be changed in the section, the representative value determination unit 220h is preferably configured so that any one of the average value, the most frequent value, and the median value of the image evaluation values of at least some of the plurality of images captured in the section is the representative value of the section. Since the variation in the evaluation value in the section where the extent of the lesion is not changed is considered to be due to the photographing condition, by setting these statistics as the representative value, the strength of the lesion in the section can be appropriately indicated.

In these embodiments, the maximum value, or any one of the average value, the most frequent value, and the median value is preferably obtained based on the evaluation values of all the images captured in the section, but as described above, when excluding the outliers from the image evaluation values as described above, it is preferable that the maximum value, or any one of the average value, the most frequent value, and the median value is obtained based on the remaining image evaluation values.

As described above, when the electronic endoscope system 1 includes the position measurement system 250 and the image-captured position information processing unit 220c, the lesion evaluation unit 220e preferably includes a section specifying unit 220i according to an embodiment. The section specifying unit 220i is configured to use the information on the image-captured position to specify the section in which section the image associated with the acquired information is captured among the plurality of sections.

According to an embodiment, the lesion evaluation unit 220e is configured to divide and evaluate the extent of the lesion in a plurality of ranks related to the strength of lesion, and it is preferable that the lesion evaluation unit 220e defines one of a plurality of ranks based on the representative evaluation value and evaluates the extent of the lesion for each section. As a result, it is possible for a surgeon to accurately know the spread and strength of the lesions that are continuously spreading in the depth direction inside the organ.

Further, according to an embodiment, it is preferable that the lesion evaluation unit 220e assesses the presence or absence of the lesion part in which the lesion extends continuously in the depth direction of the organ for each section based on the representative evaluation value. The region of the lesion part is the region in which the representative evaluation value is greater than the preset threshold value.

According to an embodiment, the lesion evaluation unit 220e can assess the presence or absence of the lesion part in which the lesion extends continuously in the depth direction of the organ based on the representative evaluation value. The region of the lesion part is the region in which the image evaluation value is greater than the preset threshold value. Since the image evaluation value is an evaluation value for each image, the image evaluation value may include a noise component. In this case, it is preferable to use the representative evaluation values for each section instead of the image evaluation value.

(Lesion Site Calculation Unit 220f)

At this time, the lesion site calculation unit 220f obtains a start position and an end position of the region of the lesion part by obtaining the section in which the lesion part is located among the above sections based on the position information on the captured image, and specifies the position of the lesion part. In order to accurately determine the start position and end position of the lesion part, it is also preferable to determine the position where the image evaluation value crosses a preset threshold value by using the image evaluation value and the information on the position where the image is captured. In this case, the lesion evaluation unit 220e compares the threshold value with each image evaluation value and assesses whether the image evaluation value crosses the threshold value. The assessment result is transmitted to the lesion site calculation unit 220f. At this time, it is preferable that the lesion evaluation unit 220e calculates the length of the lesion part from the information on the start position and the end position of the lesion part obtained by the lesion site calculation unit 220f.

Therefore, according to an embodiment, it is preferable that the monitor 300 displays at least one of the start position, the end position, and the length of the lesion part on the screen. This makes it easier for the surgeon to recognize the spread of the lesion in the depth direction of the organ.

In addition, it is preferable that the lesion evaluation unit 220e obtains the total value of the representative evaluation values corresponding to the sections included between the start position and the end position of the lesion part among the plurality of sections, and evaluates the extent of the lesion based on this total value. This makes it possible to evaluate the spread of the lesion in the depth direction of the organ and the extend (strength) of lesion (strength) at the same time. In this case, for example, the total value can be divided into a plurality of levels and the extent of the lesion can be evaluated according to the level.

The lesion evaluation unit 220e shows on the horizontal axis the position information (for example, the distance from the insertion deepest portion of the electronic scope to the opening end) along the depth direction of each section when many sections are set by shortening the length of the predetermined section, and in the graph showing the representative evaluation value on the vertical axis, the curve created by the representative evaluation values for each section may be uneven in adjacent sections. In this case, according to an embodiment, it is preferable that the curve of the representative evaluation value shown in the above graph is processed smoothly by performing moving average processing or curve fitting processing using a function indicating a predetermined curve by using the position information of the section and the representative evaluation value.

Figure 9:
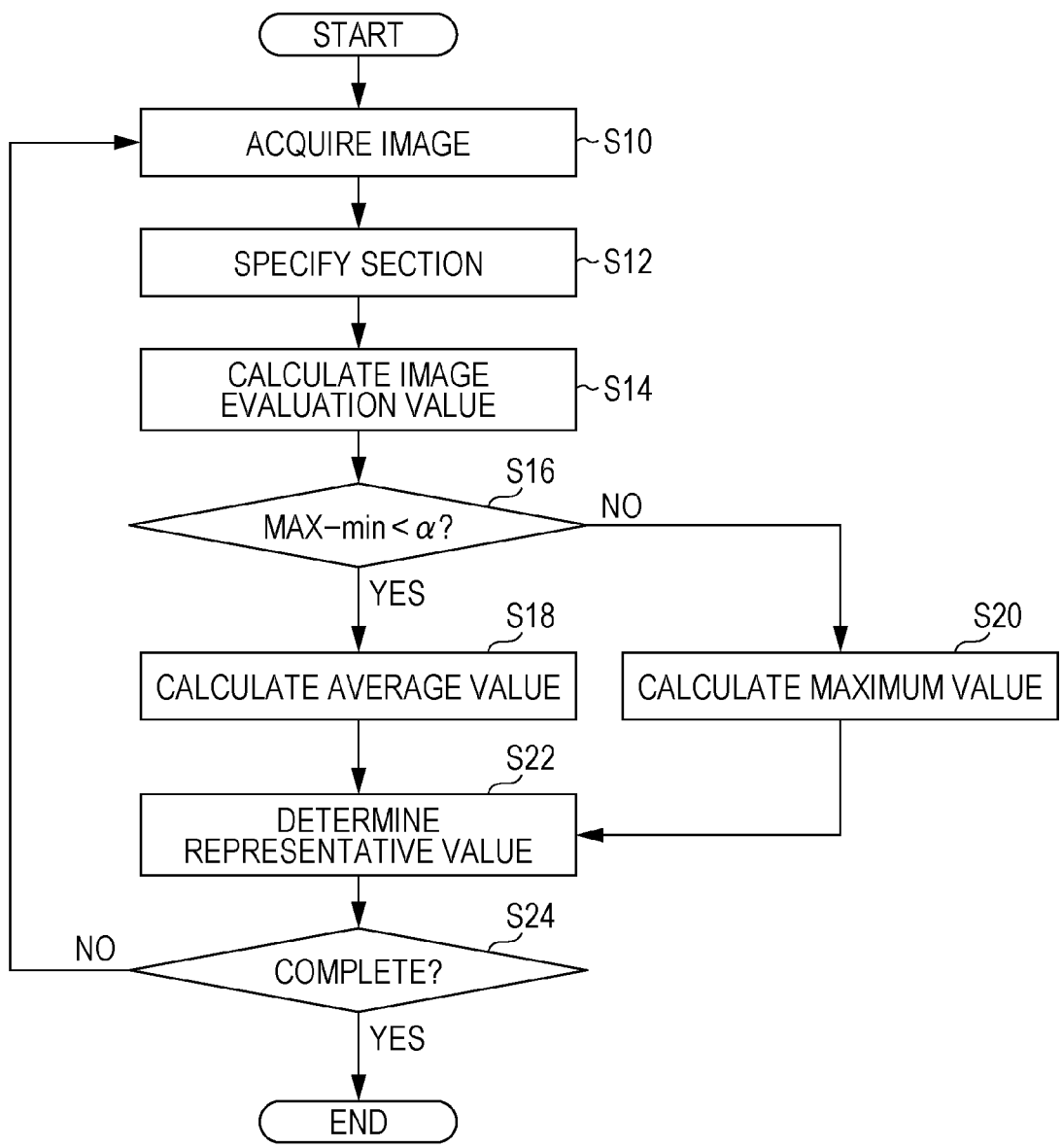
FIG. 9 is a diagram illustrating an example of a flow from image acquisition to obtaining representative evaluation values for each section performed by an evaluation unit of an embodiment.

FIG. 9 is a diagram illustrating an example of a flow from image acquisition to obtaining representative evaluation values for each section performed by an evaluation unit 221. In the example illustrated in FIG. 9, for the section in which the extent of the lesion is assessed to be changed, the maximum value of the image evaluation values corresponding to the section is used as the representative evaluation value. In addition, for the section in which the extent of the lesion is assessed not to be changed, the average value of the image evaluation values corresponding to the section is used as the representative evaluation value, but the median value or the most frequent value may be used.

First, the preprocessing unit 220a acquires an image (step S10) and performs the above-described processing. At this time, the image-captured position information processing unit 220c from the position measurement system 250 acquires the information on the image-captured position of the acquired image in association with the captured image. As a result, the lesion evaluation unit 220e uses the image-captured position information to specify the section in which the acquired image is captured in the organ among the predetermined sections (step S12). On the other hand, the image evaluation value calculation unit 220b calculates the image evaluation value using the image processed by the preprocessing unit 220a (step S14).

Note that step S14 is not limited to being performed after step S12, and can be performed before or at the same time as step S12.

The lesion evaluation unit 220e assesses whether the extent of the lesion is changed in the section based on the image evaluation value calculated for the image captured in the section. Specifically, the lesion evaluation unit 220e compares a difference ("MAX−min") between the maximum and values minimum values of the calculated image evaluation value in the section with a preset threshold value a (step S16), and when the difference is less than the threshold value (YES in step S16), the extent of the lesion is assessed not to be changed in the section, and furthermore, the average value of the image evaluation values in the section is calculated (step S18), which becomes the representative evaluation value (step S22). On the other hand, when the above difference is equal to or greater than the threshold value (NO in step S16), the lesion evaluation unit 220e assesses that the extent of the lesion is changed in the section, and furthermore, calculates the maximum value of the image evaluation values in the section (step S20), which becomes the representative evaluation value (step S22).

In the flow illustrated in FIG. 9, instead of comparing the difference between the maximum values and minimum values of the image evaluation value with the threshold value, in the assessment performed in step S16, the standard deviation or variance of the image evaluation value may be compared with the threshold value.

In this way, steps S10 to S24 are repeated until the preprocessing unit 220a finishes acquiring the image (step S24). In this way, the evaluation unit 221 obtains the representative evaluation values for each section.

Figure 10:
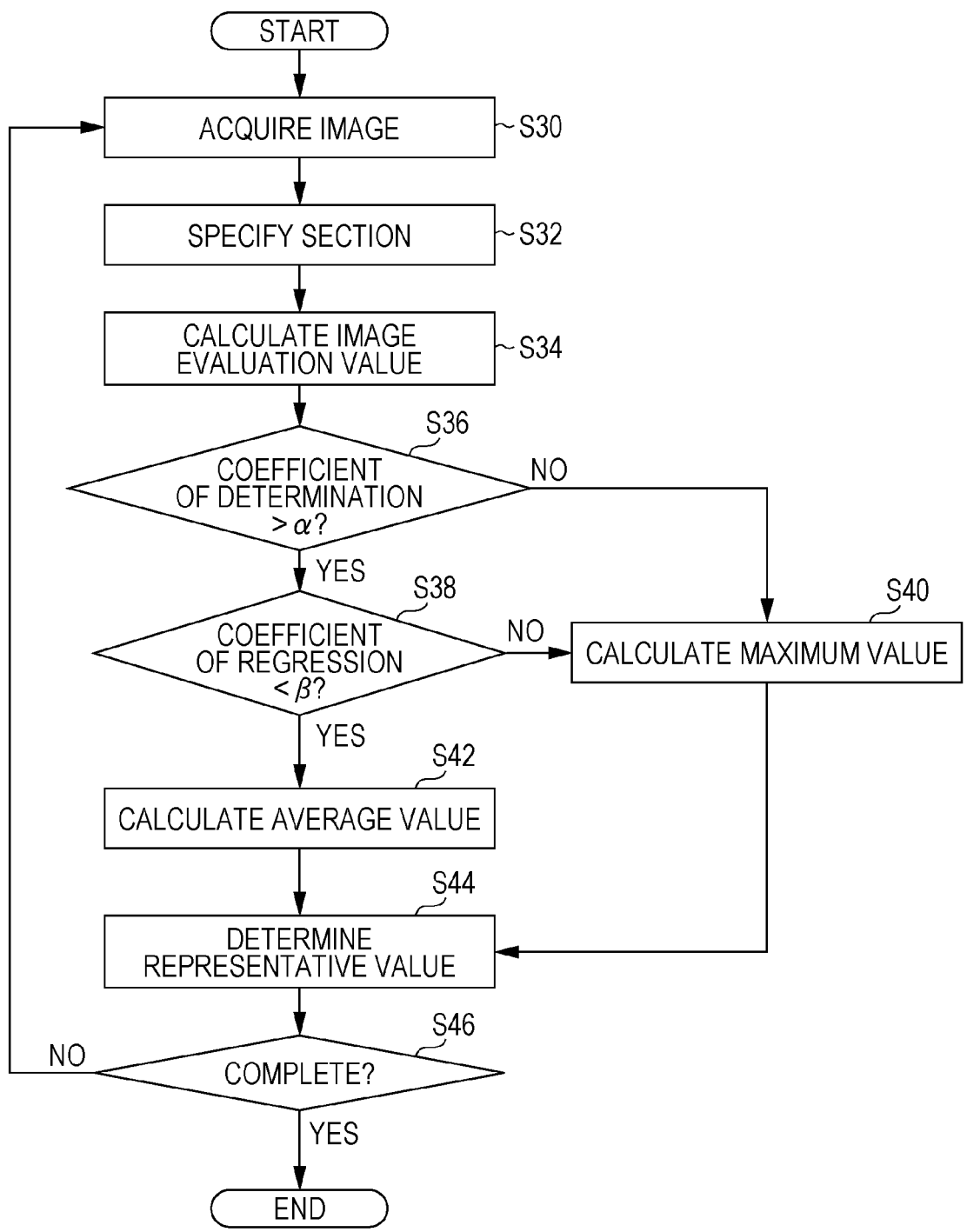
FIG. 10 is a diagram illustrating another example of a flow from the image acquisition to obtaining the representative evaluation values for each section performed by the evaluation unit of an embodiment.

FIG. 10 is a diagram illustrating an example of a flow from image acquisition to obtaining representative evaluation values for each section performed by an evaluation unit 221. Of the flows illustrated in FIG. 10, steps S30, S32, S34, S40, S42, S44, and S46 are the same as steps S10, S12, S14, S18, S20, S22, and S24 of the flow illustrated in FIG. 9.

In the flow illustrated in FIG. 10, in steps S36 and S38, it is determined in order to perform an assessment on whether the degree of change in the lesion is changed in the section.

In the lesion evaluation unit 220e, the regression line obtained by regressing the image evaluation value in the section calculated in step S34 to the image-captured position acquired from the image-captured position information processing unit 220c is obtained, and the determination coefficient is calculated. The calculated determination coefficient is compared with the preset threshold value a (step S36), when the determination coefficient exceeds the threshold value (YES in step S36), the inclination (regression coefficient) of the regression line is compared with a preset threshold value β (step S38), and when the inclination of the regression line is less than the threshold value (YES in step S38), the average value of the image evaluation value in the section is calculated (step S40), which becomes the representative evaluation value (step S44).

On the other hand, when the determination coefficient is equal to or less than the threshold value in step S36 (NO in step S36) and when the inclination of the regression line is equal to or greater than the threshold value in step S38 (NO in step S38), the maximum value of the image evaluation value in the section is calculated (step S42), which becomes the representative evaluation value (step S44).

In the flow illustrated in FIGS. 9 and 10 described above, the above-mentioned outliers may be excluded before the assessment of steps S16 and S36 is performed.

(Evaluation Result Integration Unit 220g)

The evaluation result integration unit 220g integrates, information indicating the spread of the lesion part in the depth direction, the information on the start position/the end position of the lesion part, or the length of the lesion part, and the information on the ranked strength of the lesion parts for each section, and displays the integrated information on the monitor 300 as one or more evaluation result screen in a graph showing numerical values of the representative evaluation values for each section, which is the evaluation result, or a distribution of the representative evaluation values for each section.

Figure 11:
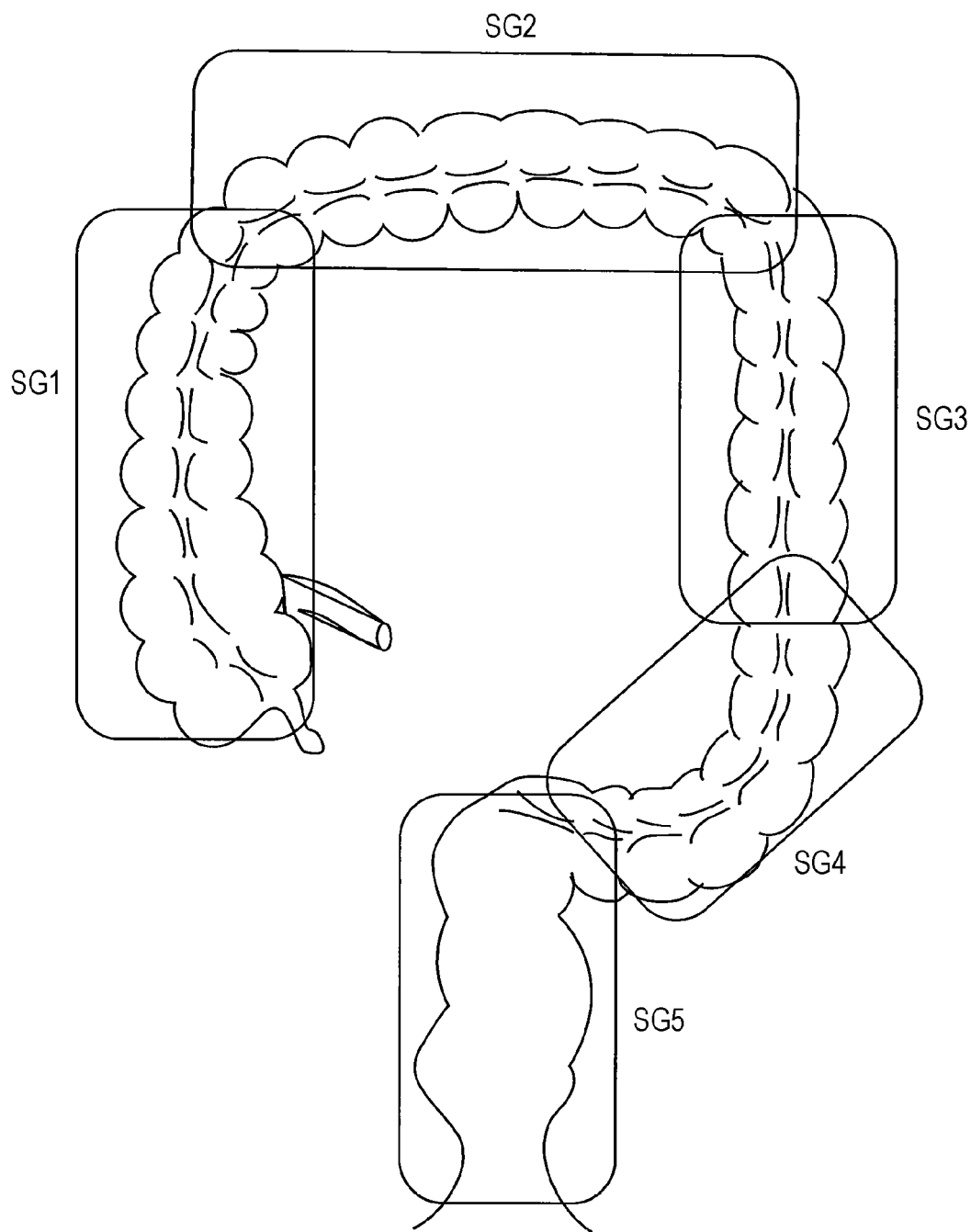
FIG. 11 is a diagram for explaining a large intestine which is an example of the organ to be measured by the endoscope system of an embodiment.

FIG. 11 is a diagram illustrating a large intestine, which is an example of an organ. The large intestine includes a rectum, sigmoid colon, descending colon, transverse colon, and ascending colon, in order from the opening end (anus). Hereinafter, the rectum is referred to as segment SG5, the sigmoid colon is referred to as segment SG4, the descending colon is referred to as segment SG3, the transverse colon is referred to as segment SG2, and the ascending colon rectum is referred to as segment SG1.

Generally, the electronic scope 100 is inserted up to the deepest portion of the segment SG1 which is the ascending colon, and then moves toward the opening end side so as to be pulled out at a substantially constant moving speed. Therefore, the electronic scope 100 captures images in the order of segment SG1, the segment SG2, the segment SG3, and . . . .

Figure 12:
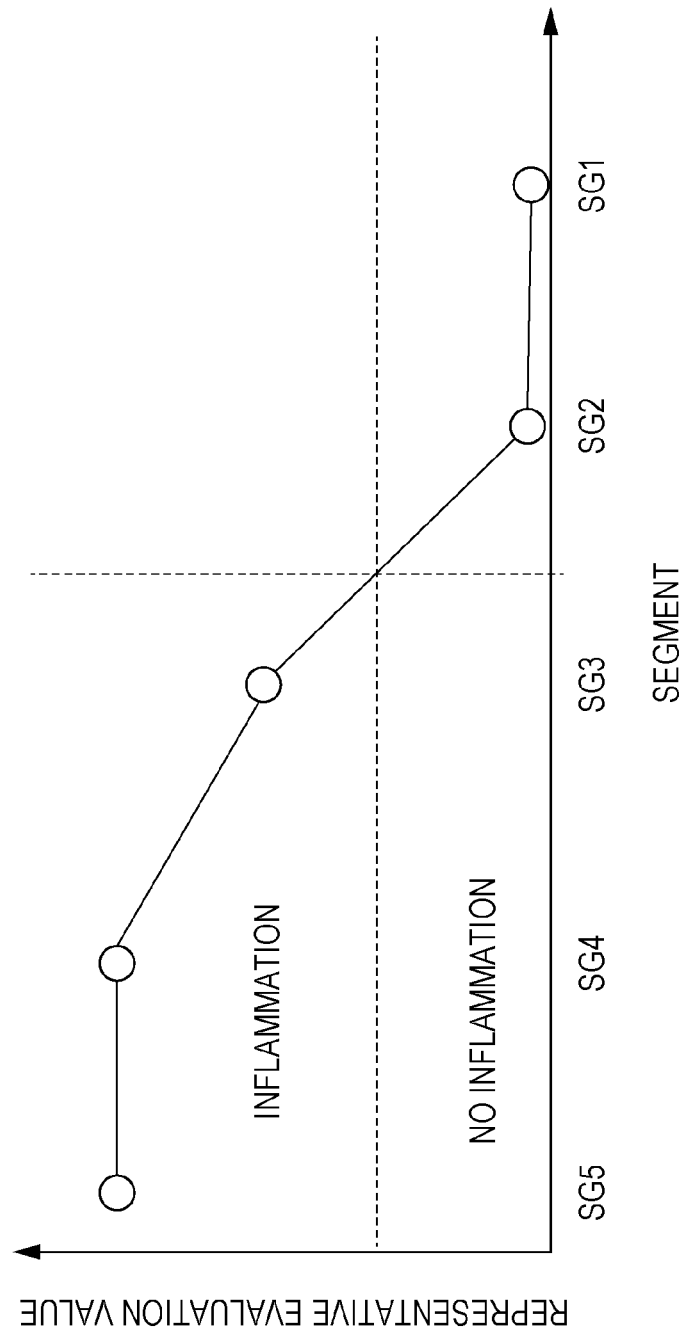
FIG. 12 is a diagram illustrating an example of an evaluation result by a lesion evaluation unit of an embodiment.

FIG. 12 is a diagram illustrating an example of the evaluation result by the lesion evaluation unit 220e. The evaluation result illustrated in FIG. 12 is a graph in which the horizontal axis represents the position from segment SG5 to segment SG1 and the vertical axis represents the integrated evaluation value. It is preferable that the number of captured images in each segment is equal. In FIG. 12, a plurality of sections are illustrated as segments SG1 to SG5, and a segment having a representative evaluation value equal to or greater than the threshold value is illustrated as a lesion part with inflammation, with the preset threshold value as a boundary. In the example illustrated in FIG. 12, it is illustrated that a part of the segment SG5, the segment SG4, and the segment SG3 causes inflammation. According to an embodiment, such an evaluation result is displayed on the monitor 300.

Figure 13:
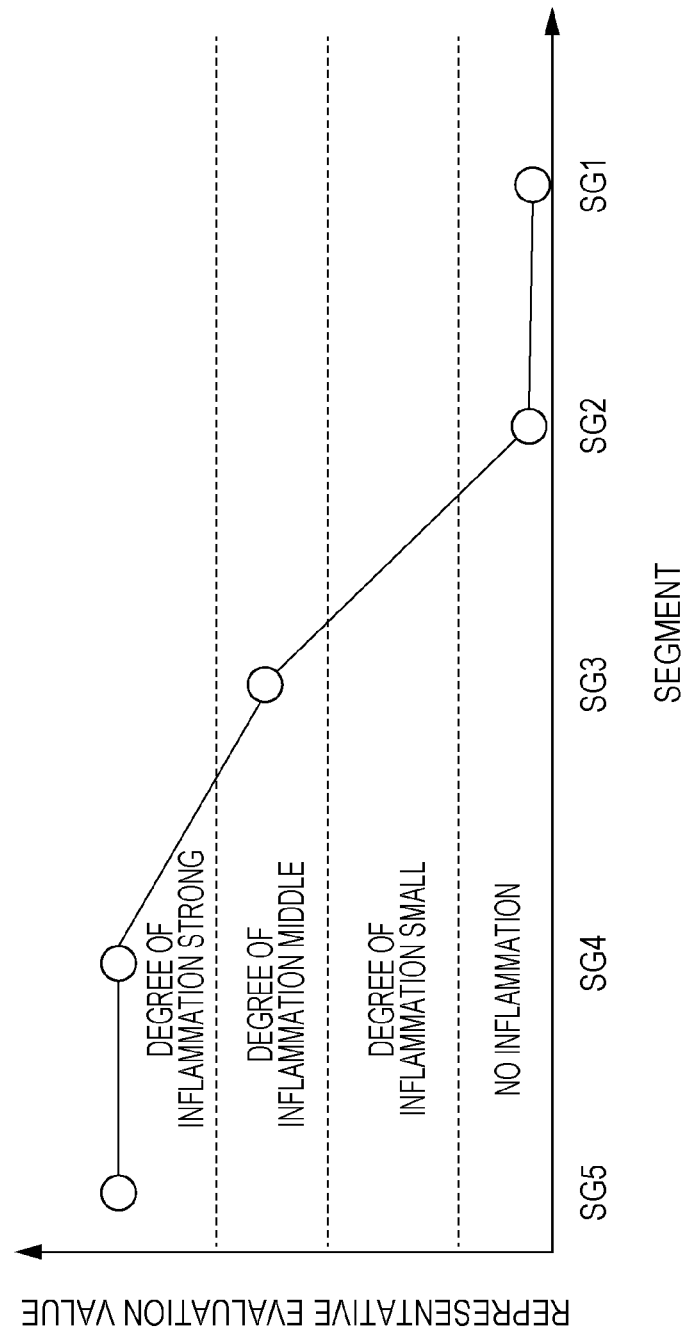
FIG. 13 is a diagram illustrating another example of the evaluation result by the lesion evaluation unit of an embodiment.

FIG. 13 is a diagram illustrating another example of the evaluation result by the lesion evaluation unit 220e. Similar to FIG. 12, the evaluation result illustrated in FIG. 13 is a graph in which the horizontal axis represents the position from the segment SG5 to the segment SG1 and the vertical axis represents the representative evaluation value. In the example illustrated in FIG. 13, the evaluation of the extent of the lesion is configured to be evaluated by a plurality of ranks related to the strength of lesion, that is, is divided and evaluated into four stages of "strong degree of inflammation", "intermediate degree of inflammation", "small degree of inflammation", and "no inflammation". The lesion evaluation unit 220e defines one of a plurality of ranks based on the representative evaluation value, and evaluates the extent of the lesions for each segment. Therefore, in the example illustrated in FIG. 13, the inflammation (lesion) exists from a part of the segment SG3 to the segment SG5, and the degree of inflammation (strength of lesion) of the segment SG5 and the segment SG4 is evaluated to be strong, and the degree of inflammation of the segment SG3 is evaluated to be intermediate. According to an embodiment, such an evaluation result is displayed on the monitor 300.

Figure 14:
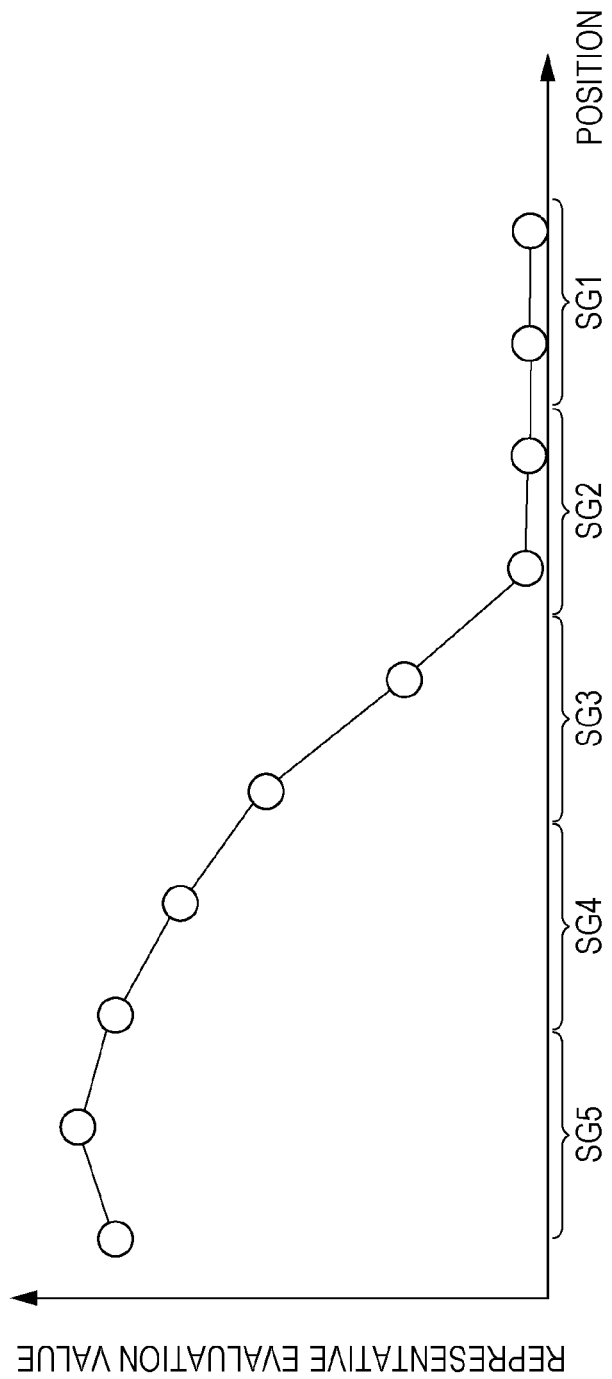
FIG. 14 is a diagram illustrating another example of the evaluation result by the lesion evaluation unit of an embodiment.

FIG. 14 is a diagram illustrating another example of the evaluation result by the lesion evaluation unit 220e. The evaluation result illustrated in FIG. 14 is a graph showing the representative evaluation value for each section, with the horizontal axis representing the position of the depth direction in the large intestine and the vertical axis representing the representative evaluation value. In FIG. 14, the section shows a narrower range than the segments SG1 to SG5, and furthermore, a section is set in which each segment is divided into two. Also in the example illustrated in FIG. 14, a section having a representative evaluation value equal to or greater than the threshold value can be defined as a lesion part with inflammation, with a preset threshold value as a boundary. According to an embodiment, such an evaluation result is displayed on the monitor 300.

As described above, the electronic endoscope system 1 preferably includes a monitor 300. According to an embodiment, it is preferable that the evaluation result integration unit 220g further integrates the presence or absence of the section in which the extent of the lesion has changed, the region in which the extent of the lesion has changed, and the degree of change, and displays the integrated one on the monitor 300 as the evaluation result screen. For example, in the evaluation result of the examples of FIG. 12 to FIG. 14, this information is added with character information indicating that, or the plot and/or the region between the plots indicating the representative evaluation value in the graph is shown in an emphasized display mode, such as a display color different from other parts. In this way, it is preferable that the monitor 300 is configured to display information on the assessment result of whether or not the extent of the lesion has changed on a screen in a different display mode when the extent of the lesion is assessed to be changed and when the extent of the lesion is assessed not to be changed.

Figure 15:
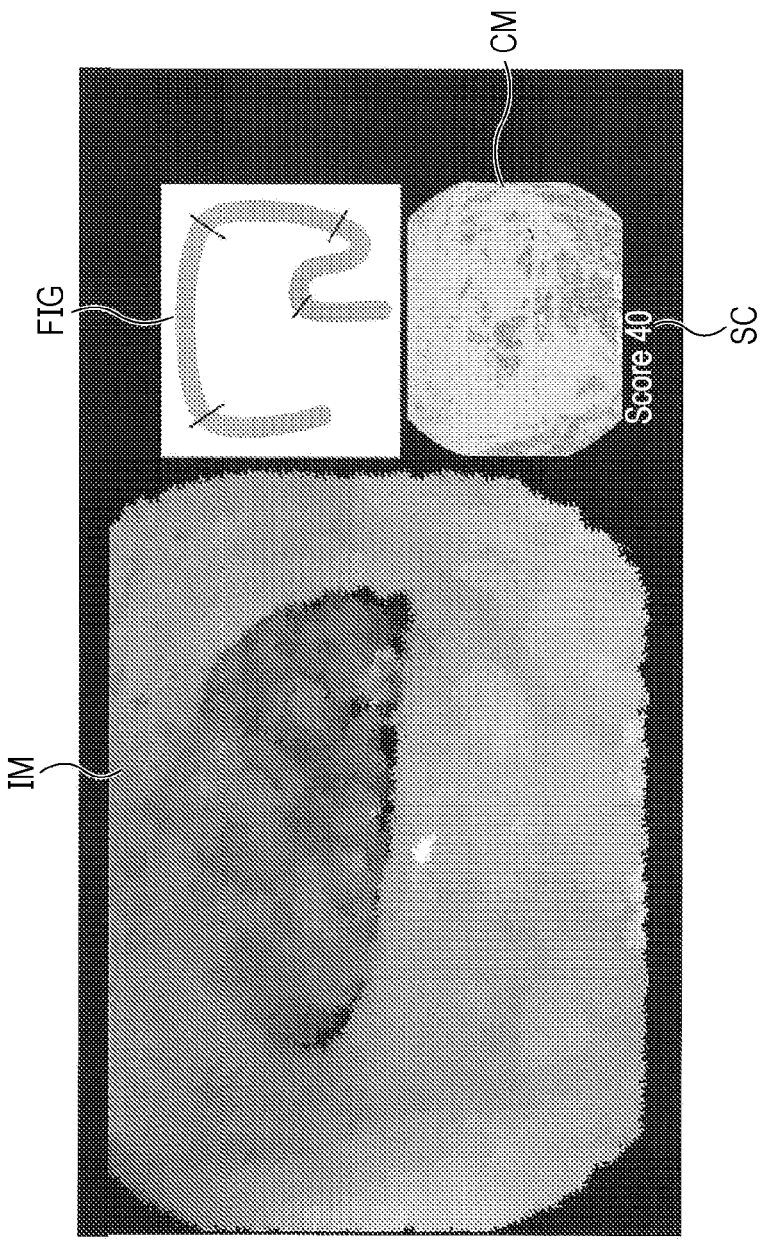
FIG. 15 is a diagram illustrating an example of a screen including one frame of a moving image displayed on a monitor of an embodiment.

FIG. 15 is a diagram illustrating an example of a screen including one frame of a moving image displayed on a monitor 300. In the example illustrated in FIG. 15, a captured image IM is shown on the left side of the screen. In the upper right of the screen, a schematic diagram FIG of a large intestine schematically showing the large intestine is shown, and in the lower upper of the screen, the image shown on the left side of the screen is shown as a color map image CM in which the color of each pixel is replaced according to the pixel evaluation value indicating the degree of inflammation, and in the lower side thereof, a score SC, which is the evaluation value of the image showing the degree of inflammation, is shown. In the example illustrated in FIG. 15, the score SC is 40. Further, in the screen example of FIG. 15, the above-mentioned information such as the section in which the extent of the lesion has changed is displayed, for example, in a display mode in which the display color in which the corresponding segment in the schematic diagram FIG of the large intestine or the region between the segments is emphasized such as display colors or the like different from other parts.

The various display screens displayed on the monitor 300 are integrated by the evaluation result integration unit 220g according to the input instruction of the surgeon, and a screen like the example illustrated in FIG. 15 is created.

The electronic endoscope system 1 described above may evaluate the extent of the lesion online when the electronic scope 100 is currently inserted inside the organ for measurement, may record the image in the memory 204 in advance, and at a later date, evaluate the spread of the lesion in the depth direction of the organ while calculating the image evaluation value, the representative evaluation value, and the like while playing back the image captured by the electronic scope 100.

At a later date, when the evaluation is performed while playing back the image captured by the electronic scope 100, it is not limited to playing back by the electronic endoscope system 1.

For example, it is possible to read the image recorded in the memory 204 to another data processing device and evaluate the spread of the lesion in the depth direction of the organ while calculating the image evaluation value, the representative evaluation value, and the like while playing back the image.

That is, the data processing device of the embodiment described later is a data processing device that processes an image of biological tissue in an organ spreading in a depth direction, the data processing device including:
an evaluation value calculation unit configured to obtain an evaluation value indicating an extent of a lesion in biological tissue of each of a plurality of images captured within a predetermined section along a depth direction of a region in the organ;
an assessment unit configured to assess whether the extent of the lesion is changed in the section based on the degree of variation of the evaluation value; and
a representative value determination unit configured to define a representative value of the section representing the evaluation value in a different method when the extent of the lesion is assessed to be changed and when the extent of the lesion is assessed not to be changed.

According to an embodiment, the data processing device may further include a monitor configured to display the information on the assessment result of whether the extent of the lesion is changed on the screen.

As described above, according to the electronic endoscope system and the data processing device, by performing the assessment on whether or not the extent of the lesion is changed in the section based on the degree of variation of the image evaluation value of the plurality of images captured in the section, it is possible to obtain an indicator (representative evaluation value) that more appropriately indicates the extent of the lesion in the section, and it is possible to accurately evaluate the extent of the lesion.

Hereinabove, although the electronic endoscope system and the data processing device of the present invention have been described in detail, the electronic endoscope system and the data processing device of the present invention are not limited to the above embodiments, and various improvements and changes may be made without departing from the gist of the present invention.

REFERENCE SIGNS LIST

1 Electronic endoscope system
100 Electronic scope
200 Processor
220 Image processing unit
220a Preprocessing unit
220b Image evaluation value calculation unit
220c image-captured position information processing unit
220d Assessment unit
220e Lesion evaluation unit
220f Lesion site calculation unit
220g Evaluation result integration unit
220h Representative value determination unit
220i Section specifying unit
230 Light source unit
300 Monitor
400 Printer
600 Server

The invention claimed is:

1. An electronic endoscope system including an endoscope configured to capture an image of biological tissue in an organ spreading in a depth direction and a processor configured to process the captured image of biological tissue, the electronic endoscope system comprising:
an evaluation value calculation unit configured to obtain an evaluation value indicating an extent of a lesion in biological tissue of each of a plurality of images captured within a predetermined section along a depth direction of a region in the organ;
an assessment unit configured to assess whether the extent of the lesion is changed in the section based on a degree of variation of the evaluation value; and
a representative value determination unit configured to define a representative value of the section representing the evaluation value in a different method when the extent of the lesion is assessed to be changed and when the extent of the lesion is assessed not to be changed.

2. The electronic endoscope system according to claim 1, wherein the assessment unit is configured to perform the assessment using an indicator indicating the degree of variation obtained from the evaluation value, and when the degree of variation indicated by the indicator is equal to or greater than a predetermined value, assess that the extent of the lesion is changed in the section.

3. The electronic endoscope system according to claim 2, wherein the indicator is a difference between a maximum value and a minimum value among the evaluation values.

4. The electronic endoscope system according to claim 2, wherein the indicator is a standard deviation or variance of the evaluation value.

5. The electronic endoscope system according to claim 2, wherein the indicator is an indicator indicating a degree of fit of regression lines in which the evaluation values are regressed in the order of the captured images.

6. The electronic endoscope system according to claim 1, further comprising:
a position information processing unit configured to associate information on the image-captured position in the organ, in which each of the images is captured, with each of the images,
wherein the assessment unit further uses the information on the image-captured position to specify the region in the section where the extent of the lesion is changed.

7. The electronic endoscope system according to claim 6, wherein the evaluation value obtained by the evaluation value calculation unit is an evaluation value indicating the extent of the lesion of the biological tissue of each of the plurality of images captured in each of the plurality of sections obtained by dividing the region in the organ including the section in depth directions, and
the electronic endoscope system further includes a section specifying unit configured to specify a section in which the image is captured among the plurality of sections by using the information on the image-captured position.

8. The electronic endoscope system according to claim 7, wherein the assessment unit is configured to perform the assessment for each section, and
the representative value determination unit is configured to define the representative values for each section.

9. The electronic endoscope system of claim 1, further comprising: a position information processing unit configured to associate information on the image-captured position in the organ, in which each of the images is captured, with each of the images,
wherein the assessment unit is configured to perform the assessment using an inclination of the regression line in which the evaluation value is regressed to the image-captured position, and when the inclination is equal to or greater than a predetermined value, assess that the extent of the lesion is changed in the section.

10. The electronic endoscope system according to claim 9, wherein the assessment unit further uses the indicator indicating the degree of fit of the regression line to perform the assessment, and when the degree of fit indicated by the indicator exceeds a predetermined value, performs the assessment using the inclination of the regression line.

11. The electronic endoscope system according to claim 9, wherein the assessment unit is configured to specify the degree of change in the lesion in the section according to a size in the inclination of the regression line.

12. The electronic endoscope system according to claim 1, wherein the assessment unit is configured to perform the assessment based on a variation in some of the evaluation values.

13. The electronic endoscope system according to claim 1, wherein the representative value determination unit is configured so that when it is assessed that the extent of the lesion is changed in the section, the maximum value of the evaluation value of at least some of the images captured in the section among the evaluation values becomes the representative value of the section.

14. The electronic endoscope system according to claim 1, wherein the representative value determination unit is configured so that when the extent of the lesion is assessed not to be changed in the section, any one of the average value, a most frequent value, and a median value of the evaluation value of at least some of the images captured in the section among the evaluation values becomes the representative value of the section.

15. The electronic endoscope system according to claim 1, further comprising: a monitor configured to display information on the assessment result of whether the extent of the lesion is changed on a screen in a different display mode when the extent of the lesion is assessed to be changed and when the extent of the lesion is assessed not to be changed.

16. A data processing device that processes an image of biological tissue in an organ that extends in a depth direction, the data processing device comprising:
an evaluation value calculation unit configured to obtain an evaluation value indicating an extent of a lesion in biological tissue of each of a plurality of images captured within a predetermined section along a depth direction of a region in the organ;
an assessment unit configured to assess whether the extent of the lesion is changed in the section based on a degree of variation of the evaluation value; and
a representative value determination unit configured to define a representative value of the section representing the evaluation value in a different method when the extent of the lesion is assessed to be changed and when the extent of the lesion is assessed not to be changed.

* * * * *